(12) United States Patent
Hlavinka et al.

(10) Patent No.: US 8,809,562 B2
(45) Date of Patent: Aug. 19, 2014

(54) USE OF METALLOCENE COMPOUNDS FOR CANCER TREATMENT

(75) Inventors: Mark L. Hlavinka, Bartlesville, OK (US); Qing Yang, Bartlesville, OK (US); Mandi Michelle Murph, Watkinsville, GA (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 7 days.

(21) Appl. No.: 13/488,490

(22) Filed: Jun. 5, 2012

(65) Prior Publication Data

US 2012/0308516 A1    Dec. 6, 2012

Related U.S. Application Data

(60) Provisional application No. 61/493,583, filed on Jun. 6, 2011.

(51) Int. Cl.

| | | |
|---|---|---|
| A61K 31/28 | (2006.01) | |
| A61K 31/695 | (2006.01) | |
| A61K 31/7068 | (2006.01) | |
| A61K 31/135 | (2006.01) | |
| A61K 31/513 | (2006.01) | |
| A61K 38/21 | (2006.01) | |
| A61K 31/415 | (2006.01) | |
| A61K 45/06 | (2006.01) | |
| A61K 31/7135 | (2006.01) | |
| A61K 31/337 | (2006.01) | |

(52) U.S. Cl.
CPC .............. *A61K 45/06* (2013.01); *A61K 2300/00* (2013.01); *A61K 31/7068* (2013.01); *A61K 31/135* (2013.01); *A61K 31/513* (2013.01); *A61K 38/21* (2013.01); *A61K 31/415* (2013.01); *A61K 31/28* (2013.01); *A61K 31/7135* (2013.01); *A61K 31/337* (2013.01); *A61K 31/695* (2013.01)

USPC ...... 556/12; 424/85.2; 424/133.1; 424/142.1; 424/85.7; 514/492; 514/63; 514/398; 514/449; 514/274; 556/11; 556/28; 556/53

(58) Field of Classification Search
CPC . A61K 2300/00; A61K 31/135; A61K 31/28; A61K 32/337; A61K 31/415; A61K 31/513; A61K 31/695; A61K 31/7068; A61K 38/21; A61K 31/7135; G01N 33/57404; G01N 33/57411; G01N 33/57415; G01N 33/57438; G01N 33/57442; G01N 33/57446
USPC .......... 424/85.2, 133.1, 142.1, 85.7; 514/492, 514/63, 398, 449, 274, 49; 556/12, 11, 28, 556/53

See application file for complete search history.

(56) References Cited

U.S. PATENT DOCUMENTS

| 4,608,387 A | 8/1986 | Kopf et al. |
| 5,002,969 A | 3/1991 | Köpf-Maier et al. |

(Continued)

FOREIGN PATENT DOCUMENTS

WO    WO 2008/034909    3/2008

OTHER PUBLICATIONS

Neidle's Cancer Drug Design and Discovery (Elsevier/Academic Press, 2008, pp. 427-431;).*

(Continued)

*Primary Examiner* — Savitha Rao
(74) *Attorney, Agent, or Firm* — Merchant & Gould P.C.

(57) ABSTRACT

Metallocene compounds and pharmaceutical compositions containing these metallocene compounds are disclosed and described. Methods of treating cancer employing such metallocene compounds and pharmaceutical compositions also are provided.

20 Claims, 4 Drawing Sheets

(56) References Cited

U.S. PATENT DOCUMENTS

| | | | |
|---|---|---|---|
| 5,296,237 A | 3/1994 | Müller et al. |
| 5,362,718 A | 11/1994 | Skotnicki et al. |
| 5,399,363 A | 3/1995 | Liversidge et al. |
| 5,439,686 A | 8/1995 | Desai et al. |
| 5,498,421 A | 3/1996 | Grinstaff et al. |
| 5,665,772 A | 9/1997 | Cottens et al. |
| 5,674,872 A | 10/1997 | Johnson |
| 6,004,973 A | 12/1999 | Guitard et al. |
| 6,096,331 A | 8/2000 | Desai et al. |
| 6,239,124 B1 | 5/2001 | Zenke et al. |
| 6,440,990 B1 | 8/2002 | Cottens et al. |
| 6,455,518 B2 | 9/2002 | Zenke et al. |
| 6,506,405 B1 | 1/2003 | Desai et al. |
| 6,537,579 B1 | 3/2003 | Desai et al. |
| 6,670,384 B2 | 12/2003 | Bandyopadhyay et al. |
| 6,749,868 B1 | 6/2004 | Desai et al. |
| 6,753,006 B1 | 6/2004 | Desai et al. |
| 6,992,035 B2 | 1/2006 | Welch et al. |
| 7,022,330 B2 | 4/2006 | Bandyopadhyay et al. |
| 7,064,225 B2 | 6/2006 | Thorn et al. |
| 7,125,899 B2 | 10/2006 | Vite et al. |
| 7,226,886 B2 | 6/2007 | Jayaratne et al. |
| 7,297,703 B2 | 11/2007 | Navarro et al. |
| 7,312,237 B2 | 12/2007 | Lee |
| 7,312,283 B2 | 12/2007 | Martin et al. |
| 7,354,579 B2 | 4/2008 | Holash et al. |
| 7,405,314 B2 | 7/2008 | Zingaro et al. |
| 7,468,452 B1 | 12/2008 | Martin et al. |
| 7,479,505 B2 | 1/2009 | Calabresi et al. |
| 7,507,749 B2 | 3/2009 | Horwitz et al. |
| 7,507,766 B2 | 3/2009 | Lazaro et al. |
| 7,517,939 B2 | 4/2009 | Yang et al. |
| 7,521,572 B2 | 4/2009 | Jayaratne et al. |
| 7,569,554 B2 | 8/2009 | Kandimalla et al. |
| 7,576,163 B2 | 8/2009 | Yang et al. |
| 7,619,047 B2 | 11/2009 | Yang et al. |
| 7,652,160 B2 | 1/2010 | Yang et al. |
| 7,820,788 B2 | 10/2010 | Desai et al. |
| 7,863,210 B2 | 1/2011 | Murray et al. |
| 7,919,639 B2 | 4/2011 | Murray et al. |
| 7,923,536 B2 | 4/2011 | Desai et al. |
| 8,012,900 B2 | 9/2011 | Murray et al. |
| 8,026,276 B2 | 9/2011 | Rubino et al. |
| 8,080,681 B2 | 12/2011 | Murray et al. |
| 8,138,229 B2 | 3/2012 | Desai et al. |
| 8,143,430 B2 | 3/2012 | Murray et al. |
| 2007/0060722 A1 | 3/2007 | Jayaratne et al. |
| 2010/0317904 A1 | 12/2010 | Small et al. |
| 2011/0082323 A1 | 4/2011 | Small et al. |

OTHER PUBLICATIONS

Tacke, Matthias, Dr., PowerPoint Presentation entitled "Novel Metallocene Anticancer Drug," presented at the IAPP Meeting, TCD, Apr. 7, 2009 in Dublin, Ireland. 10 pages.

U.S. Appl. No. 61/493,583, filed Jun. 6, 2011.

International Search Report PCT/US2012/040843, dated Aug. 17, 2012.

Alt, Helmut G., et al. ansa-Metallocenkomplexe des Typs ($C_{13}H_8$-$SiR_2$-$C_9H_{6-n}R'_n$)$ZrCl_2$ (n=0, 1; R = Me, Ph, Alkenykl; R'= Alkyl, Alkenyl): Selbstimmobilisierende Kataysatorvorstufen für die Ethylenpolymerisation, J of Organometallic Chem 562 (1998) pp. 229-253.

Alt, Helmut G., et al. Syndiospezifische Polymerisation von Propylen: 2- und 2,7-substituierte Metallocenkomplex des Typs ($C_{13}H_{8-n}R_nCR'_2C_5H_4$)$MCl_2$ (n=1,2; R = Alkoxy, Alkyl, Aryl, Hal; R'—Me, Ph; M = Zr, Hf), J of Organometallic Chem 522 (1996) pp. 39-54.

Gomez-Ruiz, Santiago, et al. Cytotoxic studies of substituted titanocene and ansa-titanocene anticancer drugs, J of Inorganic Biochem 102 (2008) pp. 1558-1570.

Strohfeldt, Katja, et al.1, Bioorganometallic Fulvene-derived titanocene anti-cancer drugs, Chem Soc Rev (2008), 37, pp. 1174-1187.

Kopf-Maier, Petra, et al., Tumorhemmung durch Metallocene: Ringsubstituierte und ringüberbrückte Titanocen-dichloride, Eur J Med Chem-Chimica Therapeutica, May-Jun. 1981 16 No. 3, pp. 275-281.

Vavere, et al. Article entitled "Preparation, Biodistribution, and Small Animal PET of $^{45}$Ti-Transferrin," published in The Journal of Nuclear Medicine, vol. 46, No. 4, Apr. 2005; pp. 683-690.

Kröger et al., Article entitled "Phase II Clinical Trial of Titanocene Dichloride in Patients with Metastatic Breast Cancer," published in Onkologie 2000; vol. 23, pp. 60-62.

Lümmen et al., Article entitled "Phase II Trial of Titanocene Dichloride in Advanced Renal-Cell Carcinoma," published in Cancer Chemother Pharmacol (1998), vol. 42; pp. 415-417.

Erxleben et al., Article entitled "Binding and Hydrolysis Studies of Antitumoural Titanocene Dichloride and Titanocene Y With Phosphate Diesters," published in Journal of Inorganic Biochemistry 104 (2010); pp. 390-396.

Christodoulou, et al., Article entitled "Anti-Proliferative Activity and Mechanism of Action of Titanocene Dichloride," published in the British Journal of Cancer (1998) vol. 77(12); pp. 2088-2097.

Korfel, et al., Article entitled "Phase I Clinical and Pharmacokinetic Study of Titanocene Dichloride in Adults With Advanced Solid Tumors," published in Clinical Cancer Research, vol. 4, Nov. 1998; pp. 2701-2708.

Harding, et al., Article entitled "Antitumour Metallocenes: Structure-Activity Studies and Interactions With Biomolecules," published in the Current Medicinal Chemistry 2000, vol. 7, pp. 1289-1303.

Bezabeh, et al., Article entitled "Detection of Drug-Induced Apoptosis and Necrosis in Human Cervical Carcinoma Cells Using $^1$H NMR Spectroscopy," published in Cell Death and Differentiation (2001), vol. 8, pp. 219-224.

Bannon et al., Article entitled "Substituted Titanocenes Induce Caspase-Dependent Apoptosis in Human Epidermoid Carcinoma Cells In Vitro and Exhibit Antitumour Activity In Vivo," published in the British Journal of Cancer (2007), vol. 97, pp. 1234-1241.

Ravera et al., Article entitled "DNA-Metallodrugs Interactions Signaled by Electrochemical Biosensors: An Overview," published in Bioinorganic Chemistry and Applications, vol. 2007, Article ID 91078, 11 pages.

Skehan, et al., Article entitled "New Colorimetric Cytotoxicity Assay for Anticancer-Drug Screening," published in Journal of the National Cancer Institute, vol. 82, No. 13, Jul. 4, 1990; pp. 1107-1112.

Hooks et al., Article entitled, "Regulators of G-Protein Signaling RGS10 and RGS17 Regulate Chemoresistance in Ovarian Cancer Cells," published in Molecular Cancer (2010), vol. 9:289; 15 pages.

Remington: The Science and Practice of Pharmacy, 21 Edition (2005), Front Cover, Inside Cover, Contents (pp. xxi and xxii), Published in the 185$^{th}$ year of the Philadelphia College of Pharmacy and Science, 4 pages.

Gómez-Ruiz, et al. entitled, "A Novel Alkenyl-Substituted ansa-Zirconocene Complex with Dual Application as Olefin Polymerization Catalyst and Anticancer Drug," published in the Journal of Organometallic Chemistry, 694 (2009) pp. 3032-3038.

Toney, et al. entitled, "Hydrolysis Chemistry of the Metallocene Dichlorides M($\eta^5$-$C_5H_5$)$_2Cl_2$, M = Ti, V, Zr. Aqueous Kinetics, Equilibria, and Mechanistic Implications for a New Class of Antitumor Agents," published in the J. Am. Chem, Soc., 1985, 107, pp. 947-953.

Allen, et al., entitled "Functionalised Cyclopentadienyl Zirconium Compounds as Potential Anticancer Drugs," published in Communication Dalton Transactions, 2008, pp. 5293-5295.

Köpf-Maier, et al., entitled "Non-Platinum-Group Metal Antitumor Agents: History, Current Status, and Perspectives" published in the American Chemical Society, 1987, 87, pp. 1137-1152.

Gómez-Ruiz et al. entitled "Anticancer Drugs Based on Alkenyl and Boryl Substituted Titanocene Complexes," published in the Journal of Organometallic Chemistry 694 (2009), pp. 1981-1987.

Claffey et al. entitled "Benzyl-Substituted Titanocene Dichloride Anticancer Drugs: From Lead to Hit," published in the Journal of Organometallic Chemistry 695 (2010), pp. 2105-2117.

Tacke et al. entitled "Novel Titanocene Anti-Cancer Drugs Derived From Fulvenes and Titanium Dichloride," published in the Journal of Organometallic Chemistry 689 (2004), pp. 2242-2249.

(56) References Cited

OTHER PUBLICATIONS

Oberschmidt et al. entitled "Antiproliferative Activity of Titanocene Y Against Tumor Colony-Forming Units," Preclinical Report published in the Anti-Cancer Drugs (2007), vol. 18, No. 3, pp. 317-321.

Kelter, et al. entitled "In-Vitro Anti-Tumor Activity Studies of Bridged and Unbridged Benzyl-Substituted Titanocenes," Preclinical Report published in the Anti-Cancer Drugs (2005), vol. 16, No. 10, pp. 1091-1098.

Köpf-Maier et al. entitled "Tumor Inhibition by Titanocene Complexes: Activity Against Sarcoma 180," published in the Anticancer Research (1986), vol. 6, pp. 33-37.

Köpf-Maier et al. entitled "Tumor Inhibition by Metallocenes: Antitumor Activity of Titanocene Dihalides $(C_5H_5)_2 TiX_2$ (X=F, Cl, Br, I, NCS) and Their Application in Buffered Solutions as a Method for Suppressing Drug-Induced Side Effects," published in the Journal of Cancer Research and Clinical Oncology, (1980), vol. 97, pp. 31-39.

\* cited by examiner

US 8,809,562 B2

USE OF METALLOCENE COMPOUNDS FOR CANCER TREATMENT

REFERENCE TO RELATED APPLICATION

This application claims the benefit of U.S. Provisional Application Ser. No. 61/493,583, filed on Jun. 6, 2011, the disclosure of which is incorporated herein by reference in its entirety.

BACKGROUND OF THE INVENTION

Despite progress in the identification and development of therapeutic agents capable of inhibiting or reducing the growth of tumors, the development of drug-resistant tumors underscores the importance of identifying and developing new drug substances for the treatment of specific cancers to improve the overall survival rate of the subject. Accordingly, it is to this end that the present disclosure is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Disclosed herein are metallocene compounds that can be used for the treatment of cancer. In some aspects, the metallocene compound can have the structure of formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof. The structures represented by these abbreviations are disclosed herein below.

In accordance with one aspect, a method of treating cancer in a subject in need thereof is provided herein. This method can comprise administering to the subject a composition comprising a therapeutically effective amount of a metallocene compound having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof, and optionally a pharmaceutically acceptable diluent, excipient, or carrier.

In accordance with another aspect, a method of inhibiting or reducing tumor growth in a subject in need thereof is provided herein. This method can comprise administering to the subject a composition comprising a therapeutically effective amount of a metallocene compound and optionally a pharmaceutically acceptable diluent, excipient, or carrier, wherein the growth of the tumor is inhibited or reduced. The metallocene compound can have formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof.

In accordance with still another aspect, a method of treating cancer in a subject in need thereof using a combination therapy is provided herein. This method can comprise administering to the subject a composition comprising a therapeutically effective amount of a metallocene compound and optionally a pharmaceutically acceptable diluent, excipient, or carrier, in combination with a therapeutically effective amount of a therapeutic agent. Suitable therapeutics agents are discussed herein below. The metallocene compound can have formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof.

In accordance with yet another aspect, pharmaceutical compositions containing a metallocene compound are provided herein. Such compositions can comprise a therapeutically effective amount of a metallocene compound having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B (i.e., one or more than one), or a pharmaceutically acceptable salt thereof, and a pharmaceutically acceptable diluent, excipient, or carrier. These pharmaceutical compositions can be, for example, pharmaceutical compositions for treating cancer in a subject in need thereof, or pharmaceutical compositions for inhibiting or reducing tumor growth in a subject in need thereof.

Additionally, this disclosure encompasses the use of a metallocene compound having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof, in the preparation of, or manufacture of, a medicament, formulation, or composition for the treatment of a cancer in a subject needing such treatment.

Both the foregoing summary and the following detailed description provide examples and are explanatory only. Accordingly, the foregoing summary and the following detailed description should not be considered to be restrictive. Further, features or variations can be provided in addition to those set forth herein. For example, certain embodiments can be directed to various feature combinations and sub-combinations described in the detailed description.

DEFINITIONS

Figure 1:
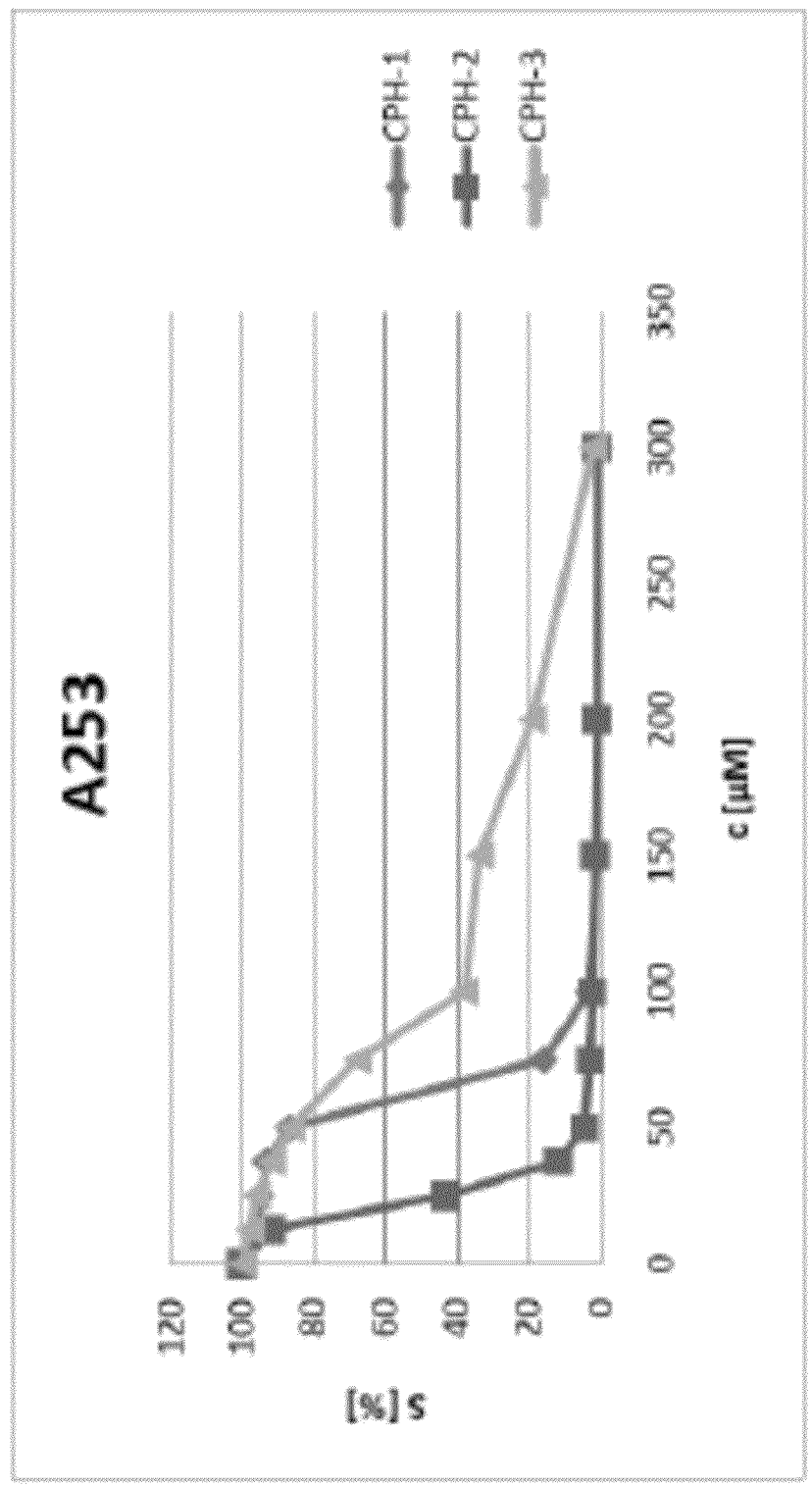
FIG. 1 presents a plot of the percentage survival of A253 head and neck tumor cells after 96 hr as a function of the respective concentration of compounds CPH-1, CPH-2, and CPH-3.

To define more clearly the terms used herein, the following definitions are provided. To the extent that any definition or usage provided by any document incorporated herein by reference conflicts with the definition or usage provided herein, the definition or usage provided herein controls.

The term "metallocene," as used herein, describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including saturated or substituted derivatives or analogs of any of these. Possible substituents on these ligands can include hydrogen, therefore partially or fully saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like, are encompassed herein.

The term "hydrocarbyl" is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, etc., derivatives or analogs thereof.

An "alkyl" group is a univalent group formed by removing a hydrogen atom from an alkane. Unless otherwise specified, alkyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers can include 2-ethyl hexyl and neooctyl.

An "alkenyl" group is a univalent group derived from an alkene by removal of a hydrogen atom from any carbon atom of an alkene. Unless otherwise specified, alkenyl groups described herein are intended to include all structural isomers, linear or branched, of a given moiety, as well as any regiochemistry or positioning of the double bond. For example, and unless otherwise specified, propen-1-yl (—CH=CHCH$_3$), propen-2-yl [(CH$_3$)C=CH$_2$], and propen-3-yl (—CH$_2$CH=CH$_2$) groups are all encompassed with a general disclosure of a propenyl group.

An "aryl" group refers to a generalized group formed by removing a hydrogen atom from an aromatic hydrocarbon ring carbon atom of an arene. One example of an "aryl" group is ortho-tolyl (o-tolyl), the structure of which is shown below:

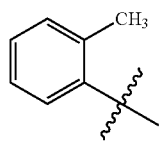

An "aralkyl" group is an aryl-substituted alkyl group having a free valance at a non-aromatic carbon atom. For example, a benzyl group is an "aralkyl" group.

This disclosure provides methods of treating cancer in a subject in need thereof. As used herein, the term "subject" refers generally to any species of mammal A mammal encompasses a primate, human, rodent, canine, feline, bovine, ovine, equine, swine, caprine, and the like, but is not limited thereto. Often, the "subject" is a human subject.

In this disclosure, "administering" (or similar terms such as administered, administration, etc.) a compound refers to providing a compound, such as one or more of the metallocene compounds disclosed herein, to a subject in need of treatment by bringing the subject in contact with, or otherwise exposing the subject to, the compound(s). The metallocene compound can be administered in a pharmaceutical composition or formulation. Modes of administration (e.g., oral, parenteral, etc.) are discussed in greater detail herein below.

The term "chemotherapy" refers to the treatment of cancer with chemical compounds that have a specific toxic effect upon the cancer, for instance, by interfering with cell reproduction.

The phrase "in combination with," when used in reference to the administration of more than one active ingredient, means either the simultaneous or sequential administration of at least two compounds, including at least one metallocene compound and at least one therapeutic agent. The compounds can be administered sequentially with each other, with the phrase "in combination with" not being limited to the order or sequence of administration, i.e., encompassing when a metallocene compound (one or more) is administered either prior to or after the administration of the therapeutic agent. A metallocene compound also can be administered in combination with a therapeutic agent when both active ingredients are administered essentially at the same time or simultaneously, including when both active ingredients are formulated in single dosage form, although this is not a requirement. For example, a metallocene compound and a therapeutic agent can be formulated into separate dosage forms or, alternatively, formulated together in a single dosage form.

In this disclosure, "cytotoxic" refers to the property of, for example, a metallocene compound or therapeutic agent to be toxic to cells, including the ability to kill a tumor cell.

The phrase "therapeutically effective amount" of a compound (metallocene compound, therapeutic agent, active ingredient, drug, etc.) refers to an amount of the compound to be administered to a subject in need of therapy or treatment which alleviates a symptom, ameliorates a condition, or slows the onset of disease conditions, according to clinically acceptable standards for the disorder or condition to be treated. For instance, a therapeutically effective amount can be an amount which has been demonstrated to have a desired therapeutic effect with statistic significance in an in vitro or in vivo clinical trial. The therapeutically effective amount can vary based on the particular dosage form, method of administration, treatment protocol, specific cancer to be treated, the benefit/risk ratio, etc., among numerous other factors.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans. Metallocene compounds described herein can be employed in a pharmaceutically acceptable salt form, and/or pharmaceutical compositions described herein can use one or more pharmaceutically acceptable diluents, excipients, or carriers; both of these concepts are discussed in greater detail herein below. Additional pharmaceutically acceptable salts, diluents, excipients, or carriers can be found in *Remington: The Science and Practice of Pharmacy*, 21st Edition (2005), which is incorporated herein by reference in its entirety.

The term "treating" is used herein, for instance, in reference to methods of treating cancer, and generally includes the administration of a compound or composition which reduces the frequency of, or delays the onset of, symptoms of a medical condition (e.g., cancer) in a subject relative to a subject not receiving the compound or composition. This can include reversing, reducing, or arresting the symptoms, clinical signs, and underlying pathology of a condition in a manner to improve or stabilize a subject's condition (e.g., regression of tumor growth).

The terms "inhibiting" or "reducing" are used in reference to methods to inhibit or to reduce tumor growth (e.g., decrease the size of a tumor) in a population as compared to a untreated control population.

The phrase "response rate" (abbreviated RR) is the sum of complete responses and partial responses by a subject to a particular therapy or treatment protocol, such as administration of a metallocene compound to a subject suffering from a type of cancer. A complete response is the disappearance of all gross evidence of disease for at least 4 weeks. A partial response is a more than 50% reduction in the product of the bidimensional measurements of each lesion maintained for at least 4 weeks. Typically, RR is measured as a percentage.

The phrase "progression-free survival" (abbreviated PFS) refers to the time from initiation of a particular therapy or treatment protocol for a subject, such as administration of a metallocene compound to a subject suffering from a type of cancer, to the earlier of (i) when disease progression is then first observed in the subject, as determined from one or more symptoms or characteristics of the subject; or (ii) death of the subject. Typically, PFS is measured in months.

The phrase "overall survival" (abbreviated OS) refers to the time from initiation of a particular therapy or treatment protocol for a subject, such as administration of a metallocene compound to a subject suffering from a type of cancer, to the death of the subject. Typically, OS is measured in months.

Although any methods, active ingredients, and other materials (e.g., excipients) similar or equivalent to those described herein can be used in the practice or testing of the invention, the typical methods, active ingredients, and other materials (e.g., excipients) are herein described.

All publications (including patents) mentioned herein are incorporated herein by reference for the purpose of describing and disclosing, for example, the constructs and methodologies that are described in the publications, which might be used in connection with the disclosure herein described. The publications discussed throughout the text are provided solely for their disclosure prior to the filing date of the present application. Nothing herein is to be construed as an admission that the Applicants are not entitled to antedate such disclosure by virtue of prior invention.

For any particular compound disclosed herein, any general or specific structure presented also encompasses all conformational isomers, regioisomers, and stereoisomers that can arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

Disclosed herein are several types of ranges. When a range of any type is disclosed or claimed, the intent is to disclose or claim individually each possible number that such a range could reasonably encompass, including end points of the range as well as any sub-ranges and combinations of sub-ranges encompassed therein. When a range of therapeutically effective amounts of an active ingredient is disclosed or claimed, for instance, the intent is to disclose or claim individually every possible number that such a range could encompass, consistent with the disclosure herein. For example, by a disclosure that the therapeutically effective amount of a metallocene compound can be in a range from about 1 mg/kg to about 50 mg/kg (of body weight of the subject), the intent is to recite that the therapeutically effective amount can be equal to about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, or about 50 mg/kg. Additionally, the therapeutically effective amount can be within any range from about 1 mg/kg to about 50 mg/kg (for example, the amount can be in a range from about 2 mg/kg to about 10 mg/kg), and this also includes any combination of ranges between about 1 mg/kg and about 50 mg/kg (for example, the amount can be in a range from about 1 mg/kg to about 5 mg/kg or from about 20 mg/kg to about 35 mg/kg). Likewise, all other ranges disclosed herein should be interpreted in a manner similar to this example.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

The terms "a," "an," and "the" are intended to include plural alternatives, e.g., at least one, unless otherwise specified. For instance, the disclosure of "a therapeutic agent" or "a metallocene compound" is meant to encompass one, or mixtures or combinations of more than one, therapeutic agent or metallocene compound, respectively.

While compositions and methods are described in terms of "comprising" various components or steps, the compositions and methods can also "consist essentially of" or "consist of" the various components or steps. For example, a pharmaceutical composition described herein can comprise; alternatively, can consist essentially of; or alternatively, can consist of; (i) a therapeutically effective amount of a metallocene compound, or a pharmaceutically acceptable salt thereof, and (ii) a pharmaceutically acceptable diluent, excipient, or carrier.

DETAILED DESCRIPTION OF THE INVENTION

The present disclosure is directed generally to metallocene compounds, pharmaceutical compositions containing metallocene compounds, methods for the treatment of cancer using metallocene compounds, and uses of metallocene compounds in the manufacture of medicaments for the treatment of cancer.

Metallocene Compounds

Pharmaceutical compositions, uses, and methods provided herein can employ a metallocene compound (one or more than one) having the structure of formula MET-A, or a pharmaceutically acceptable salt thereof:

$$E_p(Cp^A R^A_m)(Cp^B R^B_n)MX^1 X^2 \qquad \text{(MET-A)}.$$

In MET-A:
M can be Ti, Zr, or Hf;
$Cp^A$ can be a cyclopentadienyl, indenyl, or fluorenyl group;
$Cp^B$ can be an indenyl or fluorenyl group;

each $R^A$ and $R^B$ independently can be H, a halide, hydrocarbyl group, halogenated hydrocarbyl group, oxygen-containing group, sulfur-containing group, nitrogen-containing group, or silicon-containing group;

E can be a bridging group selected from:
- a bridging group having the formula $>E^{3A}R^{7A}R^{8A}$, wherein $E^{3A}$ can be C or Si, and $R^{7A}$ and $R^{8A}$ independently can be H or a hydrocarbyl group, halogenated hydrocarbyl group, oxygen-containing group, sulfur-containing group, nitrogen-containing group, or silicon-containing group;
- a bridging group having the formula $—CR^{7B}R^{8B}—CR^{2C}R^{8C}—$, wherein $R^{7B}$, $R^{8B}$, $R^{7C}$, and $R^{8C}$ independently can be H or a $C_1$ to $C_{18}$ hydrocarbyl group, or
- a bridging group having the formula $—SiR^{7D}R^{8D}—SiR^{7E}R^{8E}$, wherein $R^{7D}$, $R^{8D}$, $R^{7E}$, and $R^{8E}$ independently can be H or a $C_1$ to $C_{18}$ hydrocarbyl group;

$X^1$ and $X^2$ independently can be monoanionic ligands;
m can be 0, 1, 2, 3, 4, or 5;
n can be 0, 1, 2, 3, 4, or 5; and
p can be 0 or 1.

Within formula MET-A, M, $Cp^A$, $Cp^B$, $R^A$, $R^B$, E, $X^1$, $X^2$, m, n, and p are independent elements of the metallocene compound. Accordingly, the metallocene compound having formula MET-A can be described using any combination of M, $Cp^A$, $Cp^B$, $R^A$, $R^B$, E, $X^1$, and $X^2$ described herein, and any combination of m, n, and p described herein.

Unless otherwise specified, formula MET-A above, any other structural formulas disclosed herein, and any metallocene complex/compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In some aspects, the metal M in formula MET-A can be Ti, Zr, or Hf. For instance, M can be Ti; alternatively, M can be Zr; or alternatively, M can be Hf. In these and other aspects, $Cp^A$ can be a cyclopentadienyl group and $Cp^B$ can be an indenyl group; alternatively, $Cp^A$ can be a cyclopentadienyl group and $Cp^B$ can be a fluorenyl group; alternatively, $Cp^A$ can be an indenyl group and $Cp^B$ can be an indenyl group; alternatively, $Cp^A$ can be an indenyl group and $Cp^B$ can be a fluorenyl group; or alternatively, $Cp^A$ can be a fluorenyl group and $Cp^B$ can be a fluorenyl group.

In MET-A, each $R^A$ and/or $R^B$ independently can be H, a halide (e.g., F, Cl, Br, I), hydrocarbyl group, halogenated hydrocarbyl group, oxygen-containing group, sulfur-containing group, nitrogen-containing group, or silicon-containing group. Each $R^A$ and/or $R^B$ can be either the same or a different substituent group, and each $R^A$ and/or $R^B$ independently can be at any position on $Cp^A$ and $Cp^B$, respectively, that conforms with the rules of chemical valence.

Suitable hydrocarbyl groups can include, but are not limited to, $C_1$ to $C_{18}$ hydrocarbyl groups, $C_1$ to $C_{12}$ hydrocarbyl groups, $C_1$ to $C_{10}$ hydrocarbyl groups, $C_1$ to $C_8$ hydrocarbyl groups, and the like. For example, at least one $R^A$ and/or $R^B$ (or each $R^A$ and/or $R^B$) independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, a $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group; alternatively, a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be $R^A$ and/or $R^B$ in formula MET-A can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be $R^A$ and/or $R^B$ in formula MET-A can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be $R^A$ and/or $R^B$ in formula MET-A can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, at least one $R^A$ and/or $R^B$ in formula MET-A can be an ethenyl group, a propenyl group, a butenyl group, a pentenyl group, a hexenyl group, a heptenyl group, an octenyl group, a nonenyl group, or a decenyl group, while in another aspect, at least one $R^A$ and/or $R^B$ can be an ethenyl group, a propenyl group, a butenyl group, a pentenyl group, or a hexenyl group. For example, at least one $R^A$ and/or $R^B$ can be an ethenyl group; alternatively, a propenyl group; alternatively, a butenyl group; alternatively, a pentenyl group; or alternatively, a hexenyl group. In yet another aspect, at least one $R^A$ and/or $R^B$ can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

In an aspect, at least one $R^A$ and/or $R^B$ in formula MET-A can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, at least one $R^A$ and/or $R^B$ can be a cyclopentyl group, a substituted cyclopentyl group, a cyclohexyl group, or a substituted cyclohexyl group. Moreover, at least one $R^A$ and/or $R^B$ can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be $R^A$ and/or $R^B$ in formula MET-A.

In some aspects, the aryl group which can be $R^A$ and/or $R^B$ in formula MET-A can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be $R^A$ and/or $R^B$ in formula MET-A.

In an aspect, the substituted phenyl group which can be $R^A$ and/or $R^B$ in formula MET-A can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be the $R^A$ and/or $R^B$ group(s) in formula MET-A.

In some aspects, the aralkyl group which can be $R^A$ and/or $R^B$ in formula MET-A can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be the $R^A$ and/or $R^B$ group(s) in formula MET-A.

In an aspect, each non-hydrogen substituent(s) for the substituted cycloalkyl group, substituted aryl group, or substituted aralkyl group which can be $R^A$ and/or $R^B$ in formula MET-A independently can be, but is not limited to, a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be $R^A$ and/or $R^B$ in formula MET-A. For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

In an aspect, at least one $R^A$ and/or $R^B$ (or each $R^A$ and/or $R^B$) independently can be a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group. In another aspect, at least one $R^A$ and/or $R^B$ (or each $R^A$ and/or $R^B$) independently can be a methyl group; alternatively, an ethyl group; alternatively, a propyl group; alternatively, a butyl group; alternatively, a pentyl group; alternatively, a hexyl group; alternatively, a heptyl group; alternatively, an octyl group; alternatively, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; or alternatively, a benzyl group.

In an aspect, at least one $R^A$ and/or $R^B$ (or each $R^A$ and/or $R^B$) independently can be a $C_1$ to $C_{18}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like.

In an aspect, at least one $R^A$ and/or $R^B$ (or each $R^A$ and/or $R^B$) independently can be an oxygen-containing group having up to 18 carbon atoms, and such oxygen-containing group can contain other heteroatoms (e.g., sulfur, nitrogen, silicon) in addition to oxygen. Representative oxygen-containing groups can include, but are not limited to, alkoxy, aryloxy, aralkoxy, and -(alkyl, aryl, or aralkyl)-O-(alkyl, aryl, or aralkyl) groups, and the like. Illustrative and non-limiting examples of oxygen-containing groups which can be $R^A$ and/or $R^B$ in formula MET-A can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a nitro-phenoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), and the like. Other oxygen-containing groups which can be $R^A$ and/or $R^B$ can include, for instance, an acetate group, a trichloroacetate group, a hydrogen maleinate group, a polyol group, a polyethylene glycol (PEG) group, and more generally, can have the formula $-R^DOR^D$ or $-R^D(CO)OR^D$, wherein each $R^D$ independently can be H or any hydrocarbyl group, halogenated hydrocarbyl group, oxygen-containing group, sulfur-containing group, nitrogen-containing group, or silicon-containing group disclosed herein.

Further, oxygen-containing groups which can be $R^A$ and/or $R^B$ can have the formula $-OBR^C_2$, $-OSO_2R^C$, $-OCOCH_2NR^C_3X$, or $-OCOCH(R^C)NR^C_3X$. In these formulas, each X independently can be a halide and each $R^C$ independently can be H or a $C_1$ to $C_{18}$ hydrocarbyl group, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

In an aspect, at least one $R^A$ and/or $R^B$ (or each $R^A$ and/or $R^B$) independently can be a sulfur-containing group having up to 18 carbon atoms, and such sulfur-containing group can contain other heteroatoms (e.g., oxygen, nitrogen, silicon) in addition to sulfur. Thus, for example, certain groups can be categorized as a sulfur-containing group and an oxygen-containing group. Representative sulfur-containing groups can include, but are not limited to, a thiocarboxy group, a methylthiolate group, an ethylthiolate group, a phenylthiolate group, an alkylammonium chloride phenylthiolate group, and the like. Generally, these groups can contain up to 18 carbon atoms.

In an aspect, at least one $R^A$ and/or $R^B$ (or each $R^A$ and/or $R^B$) independently can be a nitrogen-containing group having up to 18 carbon atoms, and such nitrogen-containing group can contain other heteroatoms (e.g., oxygen, sulfur, silicon) in addition to nitrogen. Thus, for example, certain groups can be categorized as a nitrogen-containing group and a sulfur-containing group. Representative nitrogen-containing groups can include, but are not limited to, alkylaminyl, arylaminyl, aralkylaminyl, dialkylaminyl, diarylaminyl, diaralkylaminyl, -(alkyl, aryl, or aralkyl)-N-(alkyl, aryl, or aralkyl) groups, and the like. Illustrative and non-limiting examples of nitrogen-containing groups which can be $R^A$ and/or $R^B$ in formula MET-A can include, but are not limited to, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$—CH$_3$), a xylylaminyl group (—NHC$_6$H$_3$(CH$_3$)$_2$), a dimethylaminyl group (—N(CH$_3$)$_2$), a diethylaminyl group (—N(CH$_2$CH$_3$)$_2$), a di-n-propylaminyl group (—N(CH$_2$CH$_2$CH$_3$)$_2$), a di-iso-propylaminyl group (—N(CH(CH$_3$)$_2$)$_2$), a di-n-butylaminyl group (—N(CH$_2$CH$_2$CH$_2$CH$_3$)$_2$), a di-t-butylaminyl group (—N(C(CH$_3$)$_3$)$_2$), a di-n-pentylaminyl group (—N(CH$_2$CH$_2$CH$_2$CH$_2$CH$_3$)$_2$), a di-neo-pentylaminyl group (—N(CH$_2$C(CH$_3$)$_3$)$_2$), a di-phenylaminyl group (—N(C$_6$H$_5$)$_2$), a di-tolylaminyl group (—N(C$_6$H$_4$—CH$_3$)$_2$), or a di-xylylaminyl group (—N(C$_6$H$_3$(CH$_3$)$_2$)$_2$), and the like. Other nitrogen-containing groups which can be $R^A$ and/or $R^B$ can include, for instance, —N(SiMe$_3$)$_2$, —N(SiEt$_3$)$_2$, —N=C=S, etc., as well as ammonium groups (—NR$^C$$_3$X), where X can be a halide and each $R^C$ independently can be H or a $C_1$ to $C_{18}$ hydrocarbyl group, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein (e.g., methyl, ethyl, phenyl, etc.). Representative ammonium groups can include, but are not limited to, NH$_3$Br, N(Me)$_3$Cl, and the like.

In an aspect, at least one $R^A$ and/or $R^B$ (or each $R^A$ and/or $R^B$) independently can be a silicon-containing group having up to 18 carbon atoms, and such silicon-containing group can contain other heteroatoms (e.g., oxygen, sulfur, nitrogen) in addition to silicon. Thus, for example, certain groups can be categorized as a silicon-containing group and a nitrogen-containing group. Representative silicon-containing groups can include, but are not limited to, (mono)hydrocarbylsilyl, dihydrocarbylsilyl, and trihydrocarbylsilyl groups, and the like, and these groups generally can contain up to 18 carbon atoms. Illustrative and non-limiting examples of silicon-containing groups which can be $R^A$ and/or $R^B$ in formula MET-A can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

In formula MET-A, m can be 0, 1, 2, 3, 4, or 5, and n can be 0, 1, 2, 3, 4, or 5. As noted above, each $R^A$ and/or $R^B$ can be either the same or a different substituent group, and each $R^A$ and/or $R^B$ independently can be at any position on $Cp^A$ and $Cp^B$, respectively, that conforms with the rules of chemical valence. In one aspect, m can be 0, 1, or 2, and additionally or alternatively, n can be 0, 1, or 2. In another aspect, m or n can be equal to 0. In yet another aspect, m and n both can be equal to 0.

The bridging group, E, in MET-A can be a bridging group having the formula >E$^{3A}$R$^{7A}$R$^{8A}$, wherein E$^{3A}$ can be C or Si. The hydrocarbyl group, halogenated hydrocarbyl group, oxygen-containing group, sulfur-containing group, nitrogen-containing group, or silicon-containing group which independently can be R$^{7A}$ and/or R$^{8A}$ can be any hydrocarbyl group, halogenated hydrocarbyl group, oxygen-containing group, sulfur-containing group, nitrogen-containing group, or silicon-containing group disclosed herein (e.g., as pertaining to $R^A$ and $R^B$ in formula MET-A). In one aspect, for example, at least one (or both) of R$^{7A}$ and R$^{8A}$ independently can be methyl, ethyl, propyl, butyl, pentyl, hexyl, heptyl, octyl, ethenyl, propenyl, butenyl, pentenyl, hexenyl, heptenyl, octenyl, phenyl, tolyl, or benzyl. In another aspect, at least one of R$^{7A}$ and R$^{8A}$ can be a terminal alkenyl group having up to 6 carbon atoms. In yet another aspect, at least one of R$^{7A}$ and R$^{8A}$ can be a phenyl or substituted phenyl group. In a further aspect, both R$^{7A}$ and R$^{8A}$ can be phenyl groups.

The bridging group, E, in MET-A can be a bridging group having the formula —CR$^{7B}$R$^{8B}$—CR$^{7C}$R$^{8C}$—, or a bridging group having the formula —SiR$^{7D}$R$^{8D}$—SiR$^{7E}$R$^{8E}$. In these formulas, R$^{7B}$, R$^{8B}$, R$^{7C}$, R$^{8C}$, R$^{7D}$, R$^{8D}$, R$^{7E}$, and R$^{8E}$ independently can be H or a $C_1$ to $C_{18}$ hydrocarbyl group, e.g., any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein. In some aspects, R$^{7B}$, R$^{8B}$, R$^{7C}$, and R$^{8C}$ independently can be H or methyl, and R$^{7D}$, R$^{8D}$, R$^{7E}$, and R$^{8E}$ independently can be H or methyl.

While many of the metallocene compounds having formula MET-A can contain a bridge (i.e., p can be equal to 1), this is not a requirement. Certain metallocene compounds provided herein do not contain a bridge. Thus, p can be equal to 0.

In formula MET-A, $X^1$ and $X^2$ independently can be a monoanionic ligand. In some aspects, suitable monoanionic ligands can include, but are not limited to, H, BH$_4$, or a halide, hydrocarbyl group, halogenated hydrocarbyl group, oxygen-containing group, sulfur-containing group, nitrogen-containing group, or silicon-containing group. The hydrocarbyl group, halogenated hydrocarbyl group, oxygen-containing group, sulfur-containing group, nitrogen-containing group, or silicon-containing group which independently can be $X^1$ and/or $X^2$ in formula MET-A can be any hydrocarbyl group, halogenated hydrocarbyl group, oxygen-containing group, sulfur-containing group, nitrogen-containing group, or silicon-containing group disclosed herein (e.g., as pertaining to $R^A$ and $R^B$ in formula MET-A). It is contemplated that $X^1$ and $X^2$ can be either the same or a different monoanionic ligand. In one aspect, for example, at least one of $X^1$ and $X^2$ can be Cl, while in another aspect, both $X^1$ and $X^2$ can be Cl.

In another aspect of this invention, the metallocene compound can have formula MET-B, or a pharmaceutically acceptable salt thereof:

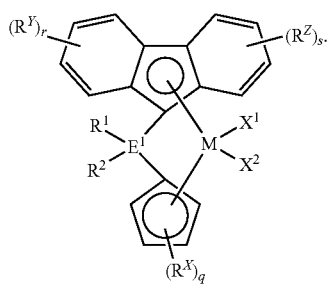

(MET-B)

In MET-B:
M can be Ti, Zr, or Hf;
each $R^X$, $R^Y$, and $R^Z$ independently can be H, a halide, hydrocarbyl group, halogenated hydrocarbyl group, oxygen-containing group, sulfur-containing group, nitrogen-containing group, or silicon-containing group;
$E^1$ can be C or Si;
$R^1$ and $R^2$ independently can be H or a hydrocarbyl group, halogenated hydrocarbyl group, oxygen-containing group, sulfur-containing group, nitrogen-containing group, or silicon-containing group;
$X^1$ and $X^2$ independently can be a monoanionic ligand; and
q, r, and s independently can be 0, 1, 2, 3, or 4.

Within formula MET-B, M, $R^1$, $R^2$, $R^X$, $R^Y$, $R^Z$, $E^1$, $X^1$, $X^2$, q, r, and s are independent elements of the metallocene compound. Accordingly, the metallocene compound having formula MET-B can be described using any combination of M, $R^1$, $R^2$, $R^X$, $R^Y$, $R^Z$, $E^1$, $X^1$, and $X^2$ described herein, and any combination of q, r, and s described herein.

The selections for M, $X^1$, and $X^2$ in formula MET-B are the same as those described herein above for formula MET-A. Each $R^X$, $R^Y$, and $R^Z$ independently can be H, a halide, hydrocarbyl group, halogenated hydrocarbyl group, oxygen-containing group, sulfur-containing group, nitrogen-containing group, or silicon-containing group, and these groups can be any halide, hydrocarbyl group, halogenated hydrocarbyl group, oxygen-containing group, sulfur-containing group, nitrogen-containing group, or silicon-containing group described herein (e.g., as pertaining to $R^A$ and $R^B$ in formula MET-A). Each $R^X$, $R^Y$, and/or $R^Z$ can be either the same or a different substituent group, and each $R^X$, $R^Y$, and/or $R^Z$ independently can be at any position on the respective ring structure in formula MET-B that conforms with the rules of chemical valence. $R^1$ and $R^2$ independently can be H or a hydrocarbyl group, halogenated hydrocarbyl group, oxygen-containing group, sulfur-containing group, nitrogen-containing group, or silicon-containing group, and these groups can be any hydrocarbyl group, halogenated hydrocarbyl group, oxygen-containing group, sulfur-containing group, nitrogen-containing group, or silicon-containing group disclosed herein (e.g., as pertaining to $R^{7A}$ and $R^{8A}$ in formula MET-A). $R^1$ and $R^2$ can be either the same or a different substituent group.

In MET-B, $E^1$ can be C, or alternatively, $E^1$ can be Si; and q, r, and s independently can be 0, 1, 2, 3, or 4. In one aspect, q, r, and s independently can be 0, 1, or 2, while in another aspect, q, r, and s independently can be 0 or 1. In these and other aspects, q can be equal to 0. Additionally or alternatively, r and s both can be equal to 0.

In addition, pharmaceutical compositions, uses, and methods provided herein can employ a metallocene compound having the structure of formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, or a pharmaceutically acceptable salt thereof, or any combination thereof (t-Bu=tert-butyl; Me=methyl; Ph=phenyl):

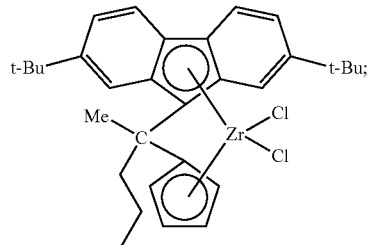

CPH-1

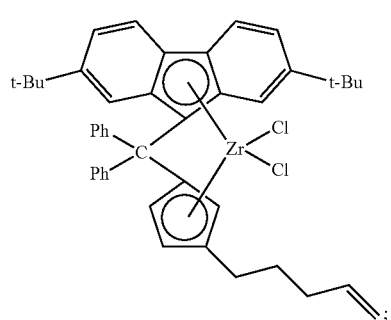

CPH-2

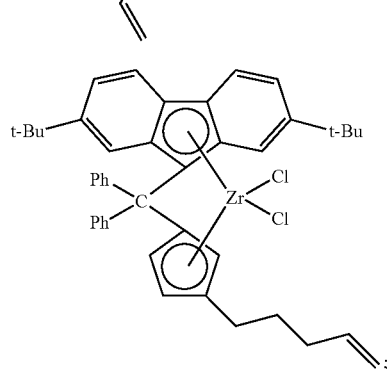

CPH-3

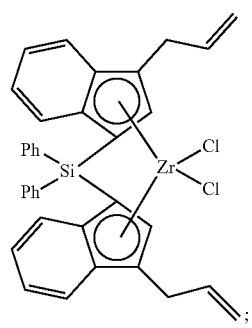

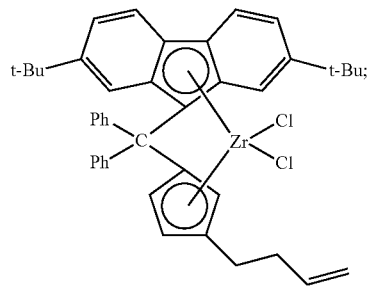

CPH-4

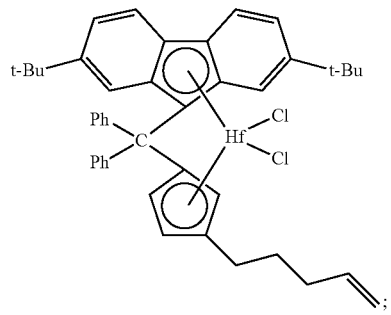

CPH-5

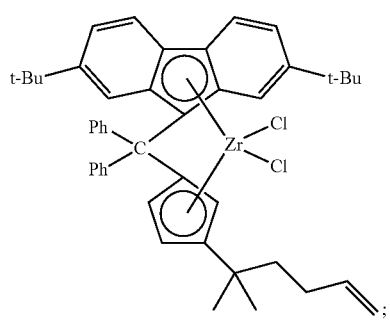
CPH-6

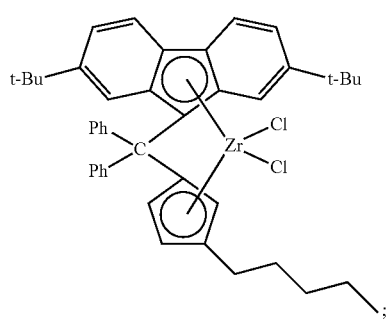
CPH-7

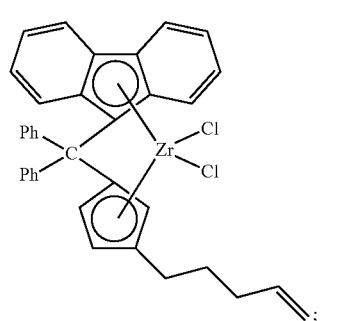
CPH-8

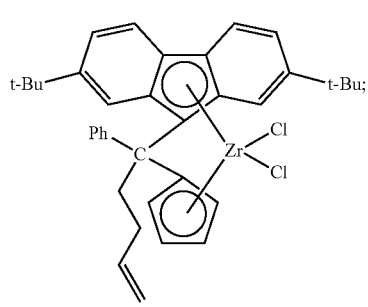
CPH-9

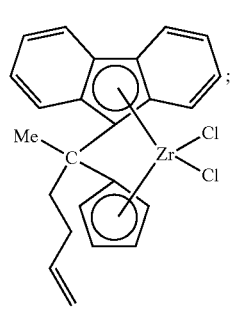
CPH-10

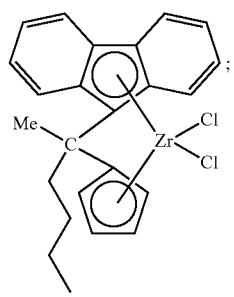
CPH-11

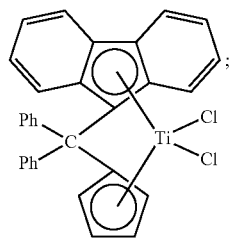
CPH-12

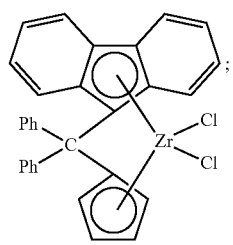
CPH-13

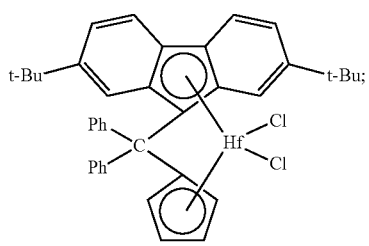
CPH-14

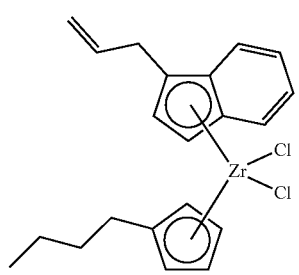
CPH-15

In certain aspects, the metallocene compound can have formula CPH-1, or a pharmaceutically acceptable salt thereof; alternatively, CPH-2, or a pharmaceutically acceptable salt thereof; alternatively, CPH-3, or a pharmaceutically acceptable salt thereof; alternatively, CPH-4, or a pharmaceutically acceptable salt thereof; alternatively, CPH-5, or a pharmaceutically acceptable salt thereof; alternatively, CPH-6, or a pharmaceutically acceptable salt thereof; alternatively, CPH-7, or a pharmaceutically acceptable salt thereof; alternatively, CPH-8, or a pharmaceutically acceptable salt thereof alternatively, CPH-9, or a pharmaceutically acceptable salt thereof; alternatively, CPH-10, or a pharmaceutically acceptable salt thereof; alternatively, CPH-11, or a pharmaceutically acceptable salt thereof; alternatively, CPH-12, or a pharmaceutically acceptable salt thereof; alternatively, CPH-13, or a pharmaceutically acceptable salt thereof; alternatively, CPH-14, or a pharmaceutically acceptable salt thereof; or alternatively, CPH-15, or a pharmaceutically acceptable salt thereof.

Metallocene compounds disclosed herein can be present in a neutral or a salt form. In cases where a metallocene compound is sufficiently acidic (or basic) to form a stable non-toxic acid (or base) salt, formulation and administration of the metallocene compound as a salt can be appropriate, and such salt forms of the metallocene compound are encompassed herein. Non-limiting examples of pharmaceutically acceptable salts include organic acid addition salts formed with acids which result in a pharmaceutically acceptable anion, for example, tosylate, methanesulfonate, acetate, citrate, malonate, tartarate, succinate, benzoate, ascorbate, and the like. Suitable inorganic salts also can be formed, and these include, but are not limited to, hydrochloride, sulfate, nitrate, bicarbonate, and carbonate salts. In the metallocene compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, it is contemplated that salt forms of these compounds can be employed.

This disclosure also contemplates and encompasses isotope substitution in the metallocene compounds, that is, increasing the isotope amount over that which occurs naturally. For instance, one or more hydrogen atoms ($^1$H) on a metallocene compound can be replaced with a deuterium atom (i.e., one or more), often abbreviated as $^2$H. Similarly, one or more carbon atoms ($^{12}$C) on a metallocene compound can be replaced with another isotope of carbon, e.g., $^{11}$C, $^{13}$C, and $^{14}$C.

Each of the metallocene compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, or CPH-15 contains two Cl ligands, and if substituents are present on the cyclopentadienyl-type groups (e.g., cyclopentadienyl, indenyl, fluorenyl), those substituents are hydrocarbyl groups (e.g., phenyl, butyl, pentenyl, etc.). As would be recognized by those of skill in the art, it can be beneficial to have a metallocene compound with improved biological medium solubility (e.g., water solubility). Accordingly, MET-A and/or MET-B include non-hydrocarbyl ligand or substituent options (i.e., containing atoms other than carbon and hydrogen), which may improve the solubility of the metallocene compound. As a representative and non-limiting example, instead of a Cl ligand (or instead of both Cl ligands), the metallocene compound can have an oxygen-containing group, sulfur-containing group, nitrogen-containing group, or silicon-containing group, and these groups can be any oxygen-containing group (e.g., an acetate group, a hydrogen maleinate group), sulfur-containing group (e.g., a thiocarboxy group), nitrogen-containing group (e.g., a hydrocarbylaminyl group, —N=C=S), or silicon-containing group (e.g., a hydrocarbylsilyl group) disclosed herein. In addition, or alternatively, an oxygen-containing group, sulfur-containing group, nitrogen-containing group, and/or silicon-containing group can be present as a substituent on the cyclopentadienyl-type group(s) and/or can be present as a substituent on the bridging atom. As representative and non-limiting examples, an oxygen-containing group or a nitrogen-containing group can be used as a substituent on the cyclopentadienyl-type group instead of a hydrocarbyl group, and such is illustrated below:

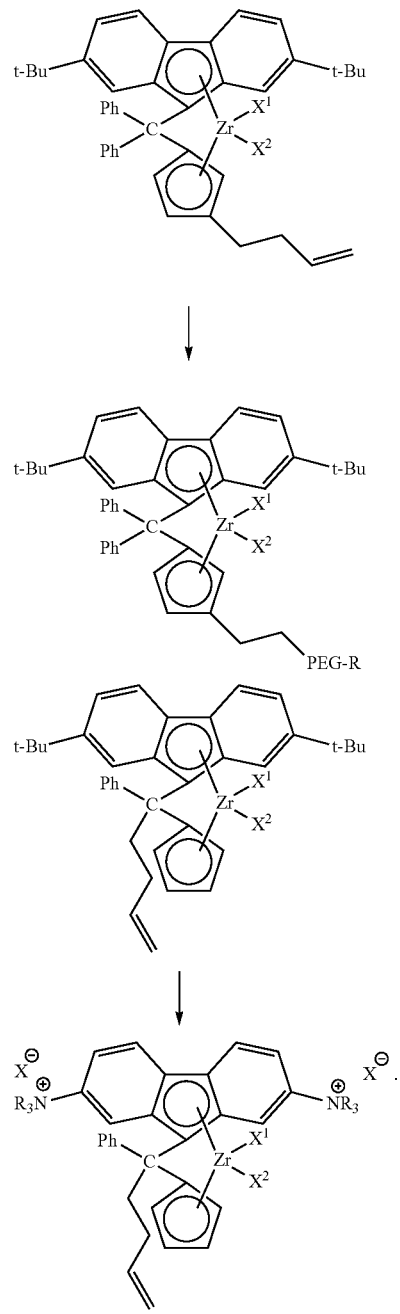

As another representative and non-limiting example, a sulfur-containing group (also an oxygen-containing group) can be used as a substituent on the carbon bridging atom instead of a hydrocarbyl group, and such is illustrated below:

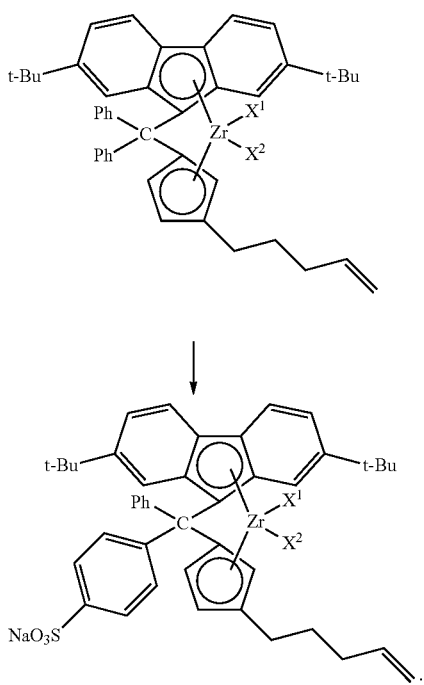

Other oxygen-containing groups, sulfur-containing groups, nitrogen-containing groups, and/or silicon-containing groups that may be present on the metallocene compounds of formula MET-A and/or MET-B in order to improve biological medium solubility are readily apparent to a skilled artisan based on the present disclosure. Additionally, any combinations of the above described groups can be used in order to improve the solubility.

Pharmaceutical Compositions and Modes of Administration

This disclosure further includes pharmaceutical compositions comprising a therapeutically effective amount of one or more metallocene compounds provided above, or a pharmaceutically acceptable salt thereof, and a pharmaceutically acceptable diluent, excipient, or carrier. Combinations and/or mixtures of more than one pharmaceutically acceptable diluent, excipient, and/or carrier can be used in these compositions. In one aspect, the pharmaceutical composition can be a pharmaceutical composition for treating cancer in a subject in need thereof, while in another aspect, the pharmaceutical composition can be a pharmaceutical composition for inhibiting or reducing tumor growth in a subject in need thereof.

In these and other aspects, the pharmaceutical compositions disclosed herein (e.g., cancer-treating compositions) can be characterized by having an $IC_{50}$ ($\mu$M) of, for example, less than 50, less than 35, less than 25, less than 20, less than 15, less than 10, or less than 5. Moreover, the pharmaceutical compositions disclosed herein can be capable of killing 50% of cancer cells within a 96 hour period, for example, within 72 hours, within 48 hours, etc.

Suitable pharmaceutical compositions can be formulated and administered to treat subjects in need by any means that contacts the metallocene compound (and optional therapeutic agent, to be discussed herein below) with the compound's site of action in or on the subject. Such compositions can be administered by any conventional means available for use in conjunction with pharmaceuticals, either as individual active ingredients or in a combination of active ingredients. The metallocene compound can be administered alone, but generally is administered with a (e.g., at least one) pharmaceutically acceptable diluent, excipient, or carrier, which is selected on the basis of, for example, the chosen route of administration, ease of formulation, and other pharmacological concerns.

Pharmaceutical compositions for use in accordance with the present disclosure can be formulated using conventional techniques and one or more pharmaceutically acceptable diluents, excipients, or carriers. Such pharmaceutical compositions can be formulated for a variety of routes of administration, including systemic and topical or localized administration. For example, suitable pharmaceutical compositions in accordance with the present disclosure can be formulated for administration in solid or liquid form including, but not limited to, (i) oral administration, for example, aqueous or non-aqueous solutions or suspensions, tablets, capsules, powders, granules, and the like; (ii) parenteral administration, for example, by subcutaneous, intramuscular, or intravenous injection as, for example, a sterile solution or suspension; or (iii) topical application, for example, as a cream, ointment, or spray applied to the skin.

Pharmaceutically acceptable wetting agents, emulsifiers, and lubricants, such as sodium lauryl sulfate and magnesium stearate, as well as pharmaceutically acceptable coloring agents, release agents, coating agents, sweetening agents, flavoring agents, preservatives, and antioxidants, can be present in the pharmaceutical composition.

Non-limiting examples of pharmaceutically acceptable antioxidants include water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations consistent with the present disclosure can include those suitable for oral, nasal, topical (including buccal and sublingual), rectal, and/or parenteral administration. The formulations can conveniently be presented in unit dosage form and can be prepared by suitable methods. The amount of active ingredient to be combined with a diluent, excipient, or carrier to produce a single dosage form can vary depending upon the individual being treated, as well as the particular mode of administration. The amount of active ingredient will generally be that amount of active ingredient which produces a therapeutic effect when administered as a single or small number of such dosage forms.

Generally, the weight percent of the active ingredient in the pharmaceutical composition can be in a range from about 0.1 percent to about 99 percent, such as, for instance, from about 0.5 percent to about 75 percent, from about 0.75 percent to about 50 percent, or from about 1 percent to about 25 percent.

Methods of preparing these formulations or compositions can include the step of contacting a metallocene compound (e.g., one or more compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B) with the diluent, excipient, or carrier and, optionally, one or more additional ingredients. Often, the formulations can be prepared by contacting the metallocene compound with liquid carriers, or finely divided solid carriers, or both, and then, if necessary, shaping the resultant product. These formulations can be further prepared shortly before administration of the active ingredient. For example, a formulation can be shaken, diluted, or dissolved, a pill divided or crushed, or a syringe filled, often in each case only a few moments before administration to the patient.

Pharmaceutical compositions suitable for oral administration can be in the form of capsules, sachets, pills, tablets, lozenges, powders, granules, or as a solution or a suspension in an aqueous or non-aqueous liquid, or as an oil-in-water or water-in-oil liquid emulsion, or as an elixir or syrup, or as a mouthwash, each containing a predetermined amount of a metallocene compound as an active ingredient.

In formulating the pharmaceutical composition for use in solid dosage forms for oral administration (e.g., capsules, tablets, pills, powders, granules, lozenges, and the like), a metallocene compound as an active ingredient can be combined with one or more of the following: (i) fillers or extenders, such as starches, lactose, sucrose, glucose, mannitol, and/or silicic acid; (ii) binders, including carboxymethylcellulose, alginates, gelatin, polyvinyl pyrrolidone, sucrose, and acacia, for instance; (iii) humectants, such as glycerol; (iv) disintegrating agents, such as agar-agar, calcium carbonate, potato or tapioca starch, alginic acid, certain silicates, and sodium carbonate; (v) solution retarding agents, such as paraffin; (vi) absorption accelerators, such as quaternary ammonium compounds; (vii) wetting agents, for example, cetyl alcohol and glycerol monostearate; (viii) absorbents, such as kaolin and bentonite clay; (ix) lubricants, such as talc, calcium stearate, magnesium stearate, solid polyethylene glycols, sodium lauryl sulfate, and combinations thereof; and (x) coloring agents. Pharmaceutical compositions also can comprise buffering agents.

Gelatin capsules can contain a metallocene compound an as active ingredient, together with powdered carriers, such as lactose, starch, cellulose derivatives, magnesium stearate, stearic acid, and the like. Similar carriers can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

A tablet can be made by compression or molding, optionally with one or more additional ingredients. Compressed tablets can be prepared using a binder (e.g., gelatin or hydroxypropylmethyl cellulose), lubricant, inert diluent, preservative, and disintegrant (e.g., sodium starch glycolate or sodium carboxymethyl cellulose), for instance, and can include various other ingredients.

Tablets and other solid dosage forms of the pharmaceutical compositions optionally can be scored or prepared with coatings and shells, such as enteric coatings and other coatings well known in the pharmaceutical arts. Formulations to provide slow or controlled release of the active ingredient—for example, using hydroxypropylmethyl cellulose, polymer matrices, liposomes, etc.—also can be produced to provide a desired release profile of the active ingredient.

Liquid dosage forms for oral administration of the pharmaceutical compositions disclosed herein can include pharmaceutically acceptable emulsions, microemulsions, solutions, suspensions, syrups, and elixirs. In addition to the active ingredient, the liquid dosage form can contain inert diluents commonly used in the art, such as, for example, water or other solvents and solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the pharmaceutical compositions for oral administration also can include adjuvants such as wetting agents, emulsifying and suspending agents, and sweetening, flavoring, coloring, perfuming, and preservative agents.

Suspensions can contain suspending agents such as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof. For buccal administration, the pharmaceutical compositions can take the form of tablets or lozenges formulated in a conventional manner for transmucosal delivery.

For administration by inhalation, a pharmaceutical composition can be delivered in the form of an aerosol spray from pressurized packs or a nebuliser, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler can be formulated containing a powder mix of the active ingredient and a suitable powder base, such as lactose or starch.

The pharmaceutical compositions can be formulated for parenteral administration by injection, e.g., by bolus injection or continuous infusion. Formulations for injection can be presented in unit dosage form, e.g., in ampoules or in multi-dose containers or vials, with an added preservative. The pharmaceutical compositions can take such forms as suspensions, solutions, or emulsions in oily or aqueous vehicles, and can contain ingredients such as suspending, buffering, stabilizing and/or dispersing agents. Alternatively, the active ingredient can be in powder form for constitution with a suitable vehicle, e.g., a lyophilized powder, which can be reconstituted with water or other solvent prior to use.

Parenteral administration, as used herein, includes modes of administration such as intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal, and the like. Pharmaceutical compositions suitable for parenteral administration can comprise one or more metallocene compounds in combination with one or more pharmaceutically acceptable sterile isotonic aqueous or non-aqueous solutions, dispersions, suspensions or emulsions, or sterile powders which can be reconstituted into sterile injectable solutions or dispersions prior to use. Moreover, a pharmaceutically acceptable diluent, excipient, or carrier can include a protein, such as albumin or human serum albumin, and the resulting pharmaceutical composition formulated for injection, as described in U.S. Pat. Nos. 7,820,788 and 7,923,536, the disclosures of which are incorporated herein by reference in their entirety.

Examples of suitable aqueous and non-aqueous carriers which can be employed in a pharmaceutical composition can include water, ethanol, polyols (such as glycerol, propylene glycol, polyethylene glycol, lactose, sucrose, glucose, mannitol, and the like, see U.S. Pat. No. 5,296,237, incorporated herein by reference in its entirety), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Buffering systems such as citrate, acetate, phosphate, and the like can be employed for pH control.

These pharmaceutical compositions also can contain adjuvants such as preservatives, wetting agents, emulsifying agents, and dispersing agents. Various antibacterial and antifungal agents, for example, paraben, chlorobutanol, phenol sorbic acid, and the like, optionally can be used. It also can be beneficial to include isotonic agents, such as sugars, sodium chloride, and the like into the pharmaceutical composition. In addition, prolonged absorption of an injectable pharmaceutical form can be accomplished by the inclusion of agents that delay absorption such as aluminum monostearate and/or gelatin.

For transmucosal or transdermal administration, penetrants appropriate to the barrier to be permeated can be used in the formulation. Such penetrants are generally known in the art, and include, for example, bile salts and fusidic acid derivatives. In addition, detergents can be used to facilitate permeation. Transmucosal administration can employ nasal sprays or suppositories. For topical administration, the pharmaceutical compositions often can be formulated into ointments, salves, gels, or creams, and the like.

Pharmaceutical compositions can be formulated for rectal administration as a suppository, which can be prepared by mixing one or more metallocene compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum cavity and release the active ingredient.

Dosage forms for the topical or transdermal administration of a metallocene compound described herein (e.g., one or more compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B) can include powders, sprays, ointments, pastes, creams, lotions, gels, solutions, patches, and inhalants.

The ointments, pastes, creams and gels can contain, in addition to the metallocene compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Buffers and preservatives also can be used.

Powders and sprays can contain, in addition to a metallocene compound described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound to the patient. Such dosage forms can be made by dissolving or dispersing a metallocene compound described herein in a proper medium. Absorption enhancers also can be used to increase the flux of the drug across the skin. The rate of such flux can be controlled by either providing a rate controlling membrane or dispersing the metallocene compound in a polymer matrix or gel.

Ophthalmic formulations, eye ointments, powders, solutions, and the like, are also contemplated and are considered within the scope of the present disclosure.

A pharmaceutical composition consistent with this disclosure also can be formulated as a sustained and/or timed release formulation. Such sustained and/or timed release formulations can be made by sustained release means or delivery devices that are well known to those of ordinary skill in the art. The pharmaceutical composition can be used to provide slow or sustained release of one or more of the active ingredients using, for example, hydroxypropylmethyl cellulose, other polymer matrices, gels, permeable membranes, osmotic systems, multilayer coatings, microparticles, nanoparticles, liposomes, microspheres, or the like, or a combination thereof to provide the desired release profile. For example, formulations containing nanoparticles of active ingredients (e.g., with an average particle size of less than 1000 nm, or less than 400 nm) are described in U.S. Pat. No. 5,399,363, the disclosure of which is incorporated herein by reference in its entirety. Suitable sustained release formulations known to those of ordinary skill in the art, including those described herein, can be readily selected for use with the pharmaceutical compositions herein described. Thus, single unit dosage forms suitable for oral administration include, but are not limited to, tablets, capsules, gelcaps, caplets, powders, and the like, and that are adapted for sustained release, also are contemplated and encompassed herein. Injectable depot forms can be made by forming microencapsulated matrices of a metallocene compound in biodegradable polymers, such as polylactide-polyglycolide. Depending on the ratio of compound to polymer, and the nature of the particular polymer employed, the rate of compound drug release can be controlled. Examples of other biodegradable polymers include poly(orthoesters) and poly(anhydrides). Depot injectable formulations also can be prepared by entrapping the compound in liposomes or microemulsions that are compatible with body tissue.

The formulations and compositions disclosed contain a therapeutically effective amount of an active ingredient (e.g., one or more metallocene compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof). The therapeutically effective amount can depend on a number of factors, such as the pharmacological characteristics of the particular compound; its mode and route of administration; the age, sex, health, weight, body surface area, etc., of the subject to be treated; the nature and extent of symptoms; the treatment protocol, including frequency and duration of treatment; and the effect desired. Exemplary therapeutically effective amounts, or dosages, include milligram amounts of the metallocene compound per kilogram of body weight of the subject ranging from about 0.001 mg/kg to about 1000 mg/kg, from about 0.01 mg/kg to about 500 mg/kg, from about 0.1 mg/kg to about 100 mg/kg, from about 1 mg/kg to about 100 mg/kg, or from about 1 mg/kg to about 50 mg/kg.

In other non-limiting examples, the therapeutically effective amount, or dose, administered to the subject can be about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 75 mg/kg, about 100 mg/kg, about 200 mg/kg, about 350 mg/kg, about 500 mg/kg, about 750 mg/kg, or about 1000 mg/kg of body weight.

The dose can be administered to the subject on an empty stomach (e.g., no food in the past 6-8 hours), with no food for at least 2 hours before, with no food for at least 1 hour before, or taken with food (substantially at the same time). The dose can be administered rapidly (e.g., all at once), or spaced out over several hours, or more. The treatment regimen can comprise administration of the metallocene compound once/day, for a period of 1 day, 2 days, 3 days, 4 days, 5 days, 6 days, or 7 days, and so forth.

In some aspects, the subject is administered more than one cycle of treatment, for instance, 2, 3, 4 or 5 cycles. In other aspects, the number of cycles is between 5 and 35 cycles, between 7 and 30 cycles, or between 10 and 25 cycles. In multi-cycle treatment protocols, the delay (or time period) between each cycle is typically 1 week or more. For instance, the time period between respective cycles can be at time intervals of about 1 week, about 2 weeks, about 3 weeks, about 4 weeks, about 5 weeks, about 6 weeks, and so forth. The treatment protocol employed during each cycle can be the same or different.

Therapeutic Agents and Combination Therapy

In accordance with an aspect of the present disclosure, a method of treating cancer in a subject in need thereof is provided. This method can comprise administering to the subject a therapeutically effective amount of a metallocene compound in combination with a therapeutically effective amount of a therapeutic agent. Hence, the metallocene compound having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt thereof, or any combination thereof, can be employed in combination therapy with other anti-tumor or anti-cancer agents (i.e., therapeutic agents). In one aspect, suitable therapeutic agents can include, but are not limited to, altretamine, busulfan, chlorambucil, cyclophosphamide, ifosfamide, mechlorethamine, melphalan, thiotepa, cladribine, fluorouracil, floxuridine, capecitabine, gemcitabine, thioguanine, pentostatin, methotrexate, 6-mercaptopurine, cytarabine, carmustine, lomustine, streptozotocin, carboplatin, cisplatin, oxaliplatin, picoplatin, iproplatin, tetraplatin, lobaplatin, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, erlotinib, idarubicin, mitoxantrone, losoxantrone, mitomycin-c, plicamycin, paclitaxel, docetaxel, topotecan, irinotecan, 9-amino camptothecan, 9-nitro camptothecan, etoposide, teniposide, vinblastine, vincristine, vinorelbine, procarbazine, asparaginase, pegaspargase, octreotide, estramustine, hydroxyurea, panorex, rituxan, daclizumab, antegren, vitaxin, therex, mylotarg, zamyl, humicade, lymphocide, trastuzumab, epratuzumab, cetuximab, pertuzumab, bevacizumab, tositumomab, ibritumomab tiuxetan, apolizumab, alemtuzumab, and the like, or a derivative, analogue, or mixture thereof.

In another aspect, suitable therapeutic agents can include, but are not limited to methotrexate, pemetrexed, cladribine, clofarabine, fludarabine, 6-mercaptopurine, nelarabine, pentostatin, capecitabine, cytarabine, 5-fluorouracil, gemcitabine, hydroxyurea, interferon, bleomycin, carmustine, lomustine, bendamustine, chlorambucil, cyclophosphamide, ifosfamide, mechlorethamine, melphalan, dacarbazine, temozolomide, procarbazine, asparaginase, bicalutamide, flutamide, fulvestrant, leuprolide acetate, megestrol acetate, tamoxifen, anastrozole, exemestane, letrozole, alemtuzumab, bevacizumab, gemtuzumab, ibritumomab tiuxetan, iodine-131 tositumomab, tositumomab, rituximab, trastuzumab, mitomycin, carboplatin, cisplatin, oxaliplatin, bortezomib, docetaxel, paclitaxel, vinblastine, vincristine, vinorelbine, daunorubicin, doxorubicin, epirubicin, irinotecan, topotecan, etoposide, teniposide, mitoxantrone, erlotinib, gefitinib, imatinib, lapatinib, sorafenib, sunitinib, and the like, or a derivative, analogue, or mixture thereof.

In yet another aspect, suitable therapeutic agents can include, but are not limited to, alemtuzumab, aminoglutethimide, anastrozole, asparginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, vorinostat, and the like, or a derivative, analogue, or mixture thereof.

In still another aspect, the therapeutic agent can comprise bevacizumab, dacarbazine, docetaxel, 5-fluorouracil, gemcitabine, ipilimumab, paclitaxel, or a mixture thereof; or alternatively, the therapeutic agent can comprise dacarbazine, paclitaxel, doxorubicin, or a mixture thereof.

The metallocene compound can precede or follow the therapeutic agent treatment by intervals ranging from less than a minute to a week or more (hence, substantially simultaneous administration is contemplated). In some aspects, the therapeutic agent (one or more) can be administered within about 1 minute, about 5 minutes, about 10 minutes, about 20 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours, prior to and/or after administering the metallocene compound. In other aspects, the therapeutic agent can be administered within about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, or about 21 days, prior to and/or after administering the metallocene compound. In some aspects, it can be beneficial to extend the time period between treatments significantly, wherein several weeks (e.g., about 1, about 2, about 3, about 4, about 5, about 6, about 7, or about 8 weeks, or more) lapse between the respective administration of the therapeutic agent and the metallocene compound.

It is contemplated that combinations of a metallocene compound with a therapeutic agent can provide synergistic benefits in cytotoxicity. For instance, the cytotoxicity of the combined treatment can be superior to the additive effect of the individual treatment of the metallocene compound and the therapeutic agent administered alone. Additionally, or alternatively, a combination of a metallocene compound with a therapeutic agent can provide acceptable cytotoxicity, but at a reduce dosage of the metallocene compound and/or the therapeutic agent. This can result in less adverse side effects during the treatment protocol, but with the same or better efficacy toward the cancer being treated.

Treatment of Cancer

Metallocene compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B, or a pharmaceutically acceptable salt, whether administered alone or in combination with another anti-tumor or anti-cancer agent (i.e., therapeutic agent) can be useful in treating a wide variety of cancers or tumors. In accordance with one aspect, a method of treating cancer in a subject in need thereof can comprise administering to the subject a composition comprising a therapeutically effective amount of the metallocene compound, or a pharmaceutically acceptable salt thereof, and optionally a pharmaceutically acceptable diluent, excipient, or carrier. In accordance with another aspect, a method of inhibiting or reducing tumor growth in a subject in need thereof can comprise administering to the subject a composition comprising a therapeutically effective amount of the metallocene compound, or a pharmaceutically acceptable salt thereof, and optionally a pharmaceutically acceptable diluent, excipient, or carrier, wherein the growth of the tumor is inhibited or reduced. In accordance with yet another aspect, the metallocene compound, or a pharmaceutically acceptable salt thereof, can be used in the preparation of, or the manufacture of, a medicament, formulation, or composition for the treatment of cancer in a subject needing such treatment.

In these and other aspects, the cancer can be brain, lung, liver, spleen, kidney, lymph node, small intestine, pancreatic, blood cell, bone, colon, stomach, urinary bladder, gall bladder, breast, endometrium, renal, prostate, testicular, ovarian, cervical, central nervous system, skin, head and neck, esophageal, or bone marrow cancer. In particular aspects provided herein, the cancer can be ovarian cancer; alternatively, testicular cancer; alternatively, head and neck cancer; alternatively, esophageal cancer; alternatively, urinary bladder cancer; alternatively, stomach cancer; alternatively, lung cancer; alternatively, small cell lung cancer; or alternatively, non-small cell lung cancer.

Furthermore, in other aspects, the cancer can be leukemia, lymphoma, or melanoma. In one aspect, the cancer can be non-Hodgkin lymphoma, while in another aspect, the cancer can be melanoma.

The cancer, in some aspects, can be resistant or insensitive to treatment with one or more of the following therapeutic agents (e.g., the cancer can be chemoresistant to): methotrexate, pemetrexed, cladribine, clofarabine, fludarabine, 6-mercaptopurine, nelarabine, pentostatin, capecitabine, cytarabine, 5-fluorouracil, gemcitabine, hydroxyurea, interferon, bleomycin, carmustine, lomustine, bendamustine, chlorambucil, cyclophosphamide, ifosfamide, mechlorethamine, melphalan, dacarbazine, temozolomide, procarbazine, asparaginase, bicalutamide, flutamide, fulvestrant, leuprolide acetate, megestrol acetate, tamoxifen, anastrozole, exemestane, letrozole, alemtuzumab, bevacizumab, gemtuzumab, ibritumomab tiuxetan, iodine-131 tositumomab, tositumomab, rituximab, trastuzumab, mitomycin, carboplatin, cisplatin, oxaliplatin, bortezomib, docetaxel, paclitaxel, vinblastine, vincristine, vinorelbine, daunorubicin, doxorubicin, epirubicin, irinotecan, topotecan, etoposide, teniposide, mitoxantrone, erlotinib, gefitinib, imatinib, lapatinib, sorafenib, and/or sunitinib.

In other aspects, the cancer can be resistant or insensitive to treatment with one or more of the following therapeutic agents: alemtuzumab, aminoglutethimide, anastrozole, asparaginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, and/or vorinostat.

In a further aspect, the cancer can be resistant or insensitive to treatment with a platinum agent, and/or the cancer can be resistant or insensitive to treatment with a taxane, and/or the cancer can be resistant or insensitive to treatment with dacarbazine. For example, the cancer can be SKOV-3 ovarian cancer; alternatively, the cancer can be Hey-A8 MDR ovarian cancer; alternatively, the cancer can be T-24 urinary bladder cancer; or alternatively, the cancer can be MeWo melanoma.

It is contemplated that the administration of a metallocene compound (e.g., one or more compounds having formula CPH-1, CPH-2, CPH-3, CPH-4, CPH-5, CPH-6, CPH-7, CPH-8, CPH-9, CPH-10, CPH-11, CPH-12, CPH-13, CPH-14, CPH-15, MET-A, and/or MET-B) can result in an increase in the progression-free survival (PFS)—as compared to a control group not receiving the cytotoxic agent—of between 1 month and about 24 months; alternatively, from about 2 months to about 18 months; or alternatively, from about 2 months to about 12 months.

Likewise, the administration of such metallocene compounds can result in an increase in the overall survival (OS)— as compared to control group not receiving the cytotoxic agent—of between about 2 months and about 48 months; alternatively, from about 3 months to about 36 months; or alternatively, from about 4 months to about 24 months.

The administration of the metallocene compound can result in an overall response rate (RR) in a range from about 10% to about 75%, from about 10% to about 60%, or from about 10% to about 50%.

The cytotoxic activity of the metallocene compound can be evaluated using numerous clinical methodologies. For instance, cytoxicity can be evaluated in vitro against various human cancer cell lines, e.g., ovarian cell line, colon tumor cell line, prostate tumor cell line, leukemia cell line, etc. Cytotoxicity also can be assessed using in vivo testing, such as by the implantation of various cancer or tumor models in mice (e.g., leukemia, lung cancer, prostate cancer, colon cancer, breast cancer, melanoma, etc.), and subsequently administering a therapeutically effective amount of a respective metallocene compound to the mice.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

Examples 1-5

Evaluation of the Cytotoxicity of Metallocene Compounds CPH-1, CPH-2, and CPH-3 in Various Tumor Cell Lines Drug solutions of CPH-1, CPH-2 and CPH-3 were made in dimethyl sulfoxide (DMSO, Sigma Aldrich) at a concentration of 20 mM, filtered through a Millipore filter, 0.22 μm, before use, and diluted by nutrient medium to various working concentrations. The nutrient medium was RPMI-1640 (PAA Laboratories) supplemented with 10% fetal bovine serum (Biochrom AG) and penicillin/streptomycin (PAA Laboratories).

The cell line A253, A549, and A2780 cultures were maintained as monolayer in RPMI 1640 (PAA Laboratories, Pasching, Germany) supplemented with 10% heat inactivated fetal bovine serum (Biochrom AG, Berlin, Germany) and penicillin/streptomycin (PAA Laboratories), at 37° C. in a humidified atmosphere of 5% (v/v) $CO_2$.

The cytotoxic activities of CPH-1, CPH-2 and CPH-3 were evaluated using a sulforhodamine-B (SRB, Sigma Aldrich) microculture colorimetric assay, as described in Skehan et al., *J. Natl. Cancer I.* 82 (1990) 1107-1112, the disclosure of which is incorporated herein by reference in its entirety. In short, exponentially growing cells were seeded into 96-well plates on day zero at the appropriate cell densities to prevent confluence of the cells during the period of experiment. After 24 hr, the cells were treated with serial dilutions of the compounds CPH-1, CPH-2, and CPH-3 for 96 hr. Final concentrations achieved in treated wells were 12.5, 25, 37.5, 50, 75, 100, 150, 200 and 300 mmol/L. Each concentration was tested in three triplicates on each cell line. The final concentration of DMSO solvent never exceeded 0.5%, which was non-toxic to the cells. The percentages of surviving cells relative to untreated controls were determined 96 hr after the beginning of drug exposure. After 96 hr treatment, the supernatant medium from the 96 well plates was thrown away and the cells were fixed with 10% TCA. For a thorough fixation, plates were then allowed to stand at 4° C. After fixation, the cells were washed in a strip washer. The washing was carried out four times with water using alternate dispensing and aspiration procedures. The plates were then dyed with 100 μL of 0.4% SRB for about 45 min. After dyeing, the plates were again washed to remove the dye with 1% acetic acid and allowed to air dry overnight. 100 μL of 10 mM Tris base solutions were added to each well of the plate, and absorbance was measured at 570 nm using a 96 well plate reader (Tecan Spectra, Crailsheim, Germany). The $IC_{50}$ values, defined as the concentration of the compound at which 50% cell inhibition was observed after 96 hr, were estimated from dose-response curves.

Figure 2:
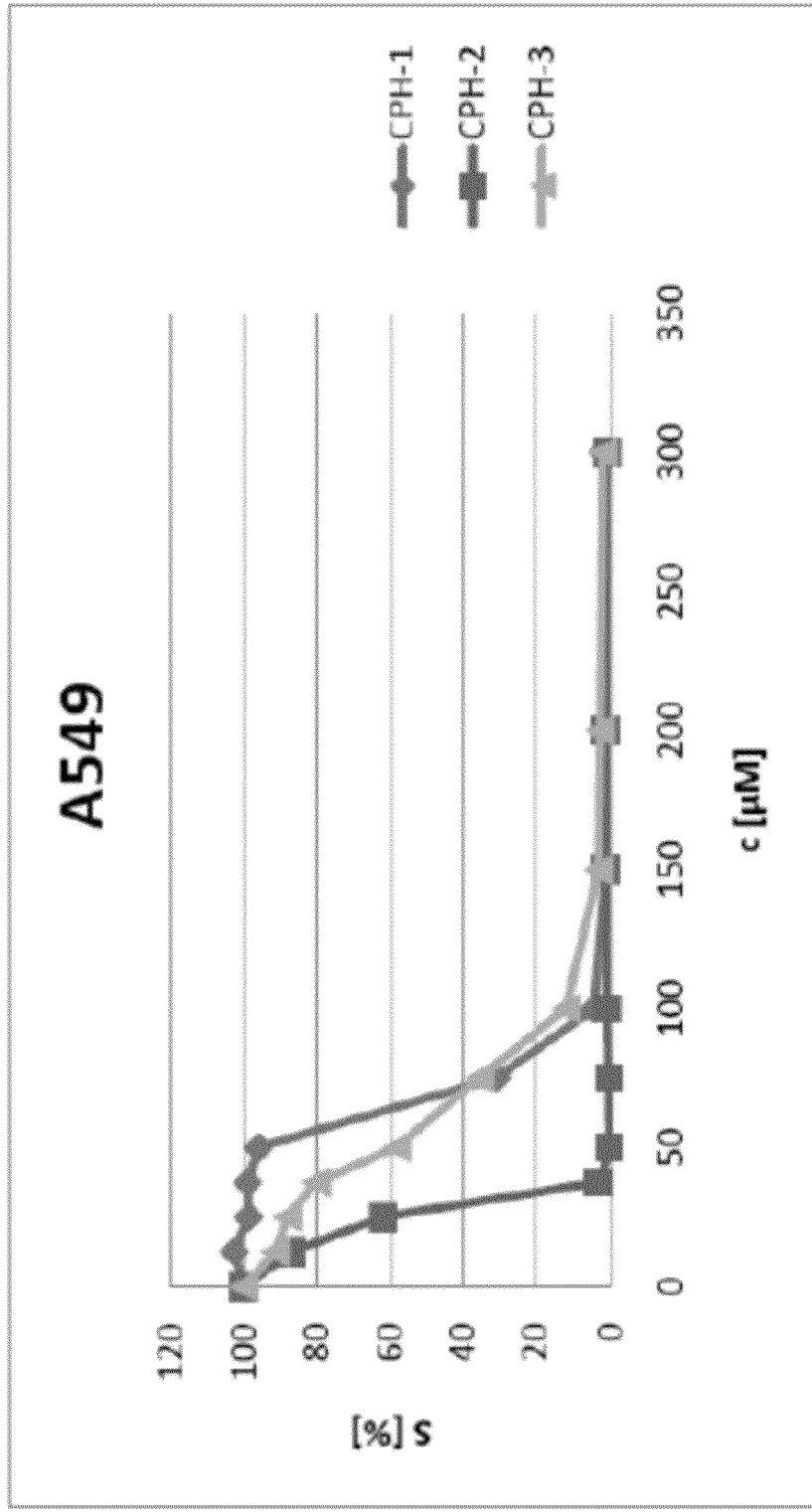
FIG. 2 presents a plot of the percentage survival of A549 lung carcinoma cells after 96 hr as a function of the respective concentration of compounds CPH-1, CPH-2, and CPH-3.
Figure 3:
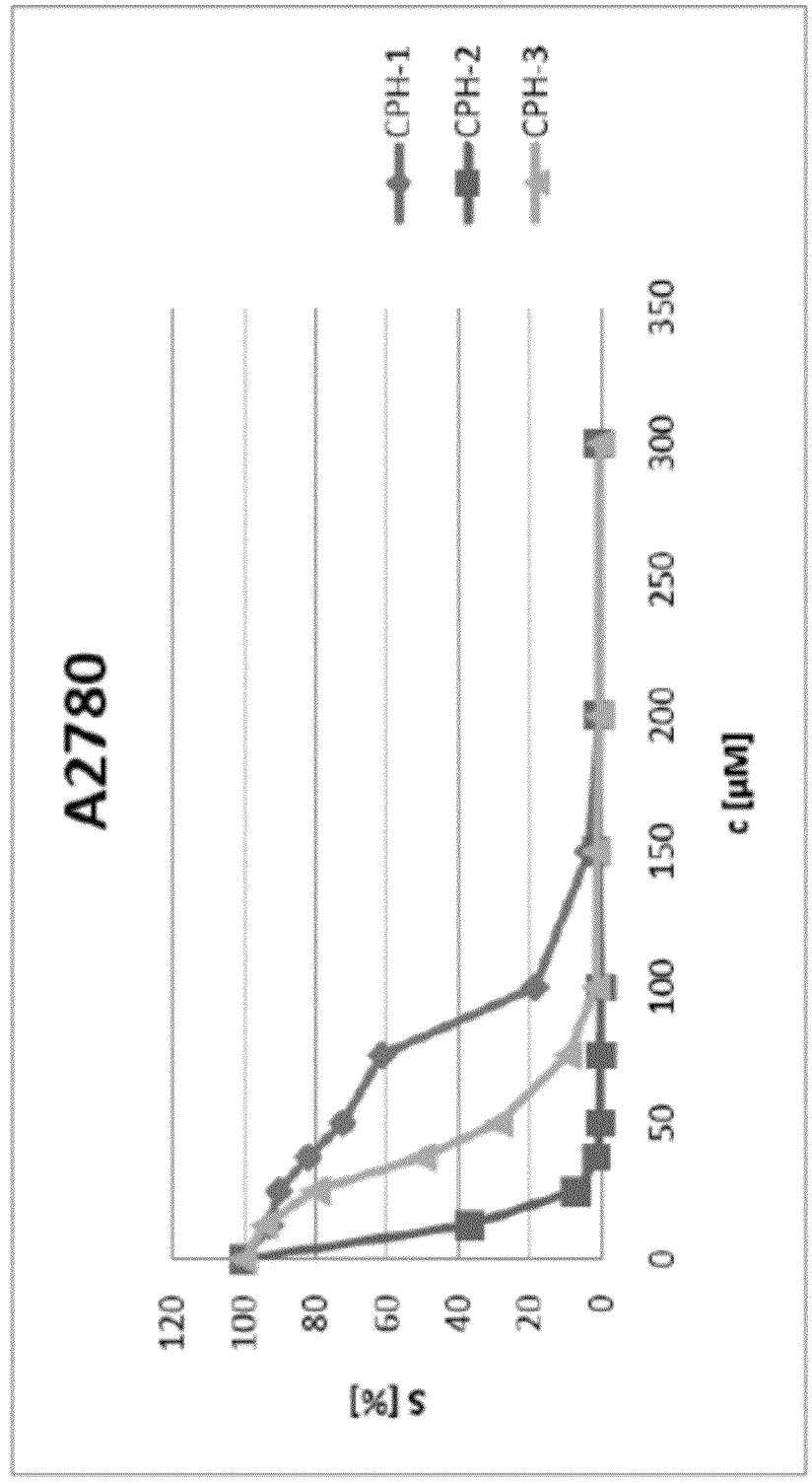
FIG. 3 presents a plot of the percentage survival of A2780 ovarian cancer cells after 96 hr as a function of the respective concentration of compounds CPH-1, CPH-2, and CPH-3.
Figure 4:
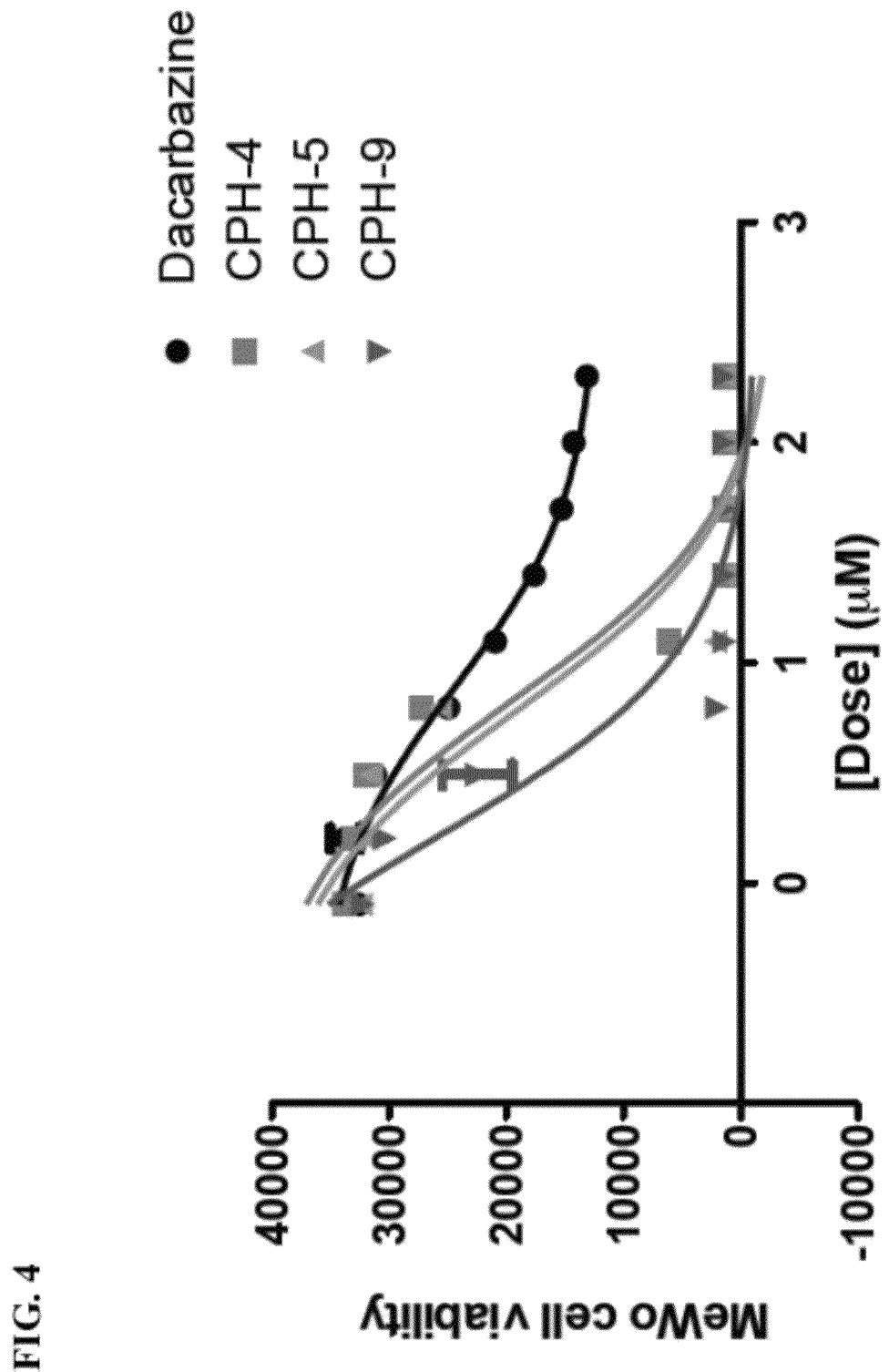
FIG. 4 presents a plot of the MeWo melanoma cancer cell viability after 96 hr as a function of the respective concentration of dacarbazine, CPH-4, CPH-5, and CPH-9.

Table I summarizes the cytotoxicity test results of compounds CPH-1 (Example 1), CPH-2 (Example 2), and CPH-3 (Example 3) against the tumor cell lines A253 (head and neck tumor), A549 (lung carcinoma) and A2780 (ovarian cancer). Results for Comparative Example 4 (titanocene=bis cyclopentadienyl titanium dichloride) and Comparative Example 5 (cisplatin) also are included in Table I. FIGS. 1-3 illustrate the percentage survival (S) of A253 cells, A549 cells, and A2780 cells, respectively, grown for 96 hr in the presence of increasing concentrations of compounds CPH-1, CPH-2, and CPH-3.

As illustrated in Table I and FIGS. 1-3, each of compounds CPH-1, CPH-2, and CPH-3 was active against the various cancer cell lines. Compound CPH-2 was the most active of CPH-1, CPH-2, and CPH-3, and had an unexpectedly superior $IC_{50}$ value of 10.5 μM against A2780 ovarian cancer.

TABLE I

Comparison of $IC_{50}$ of Examples 1-5 for A253, A549, and A2780.

| | | $IC_{50} \pm SD$ (μM) | | |
|---|---|---|---|---|
| Example | Compound | A253 | A549 | A2780 |
| 1 | CPH-1 | 62.83 ± 0.97 | 68.69 ± 0.62 | 77.89 ± 8.06 |
| 2 | CPH-2 | 22.21 ± 0.15 | 26.62 ± 0.81 | 10.50 ± 0.16 |
| 3 | CPH-3 | 97.54 ± 7.31 | 59.73 ± 2.41 | 38.18 ± 0.58 |
| 4 | Titanocene | 188.71 ± 6.36 | 167.62 ± 3.31 | N/A |
| 5 | Cisplatin | 0.81 ± 0.02 | 1.51 ± 0.02 | 0.55 ± 0.03 |

Examples 6-13

Evaluation of the Cytotoxicity of Metallocene Compounds CPH-4, CPH-5, CPH-6, CPH-7, CPH-8, CPH-9, CPH-10, and CPH-11 in Various Tumor Cell Lines Drug solutions of CPH-4, CPH-5, CPH-6, CPH-7, CPH-8, CPH-9, CPH-10, and CPH-11 were prepared and tested using substantially the same procedure as described in Examples 1-5. Table II summarizes the cytotoxicity test results of these metallocene compounds against the tumor cell lines A253 (head and neck tumor), A549 (lung carcinoma) and A2780 (ovarian cancer).

As illustrated in Table II, each of the metallocene compounds was active against the various cancer cell lines. Generally, these compounds resulted in higher cytotoxicity against the A253 and A2780 cell lines than against the A549 cell line. However, CPH-5 and CPH-7 performed well against all of the studied cancer lines, with average $IC_{50}$ values ranging from about 9 to about 28 μM.

Unexpectedly, CPH-4, CPH-6, and CPH-9 showed remarkably high activity against the A253 cancer cell line, each with average $IC_{50}$ values of less than 8.5 μM. Also unexpectedly, in addition to CPH-2 (Example 2), compounds CPH-5, CPH-7, and CPH-8 showed remarkably high activity against the A2780 cancer cell line, each with average $IC_{50}$ values of less than 12.5 μM. While not wishing to be bound by theory, Applicants believe that these results represent the highest cytotoxic activity reported for metallocene complexes for the A253 and the A2780 cancer cell lines.

TABLE II

Comparison of $IC_{50}$ of Examples 6-13 for A253, A549, and A2780.

| | | $IC_{50} \pm SD$ (μM) | | |
|---|---|---|---|---|
| Example | Compound | A253 | A549 | A2780 |
| 6 | CPH-4 | 6.96 ± 2.84 | 47.97 ± 1.57 | 15.17 ± 0.95 |
| 7 | CPH-5 | 12.07 ± 2.01 | 15.35 ± 0.42 | 9.83 ± 1.72 |
| 8 | CPH-6 | 8.24 ± 0.47 | 100.68 ± 5.29 | 30.83 ± 2.88 |
| 9 | CPH-7 | 11.51 ± 0.39 | 28.39 ± 0.61 | 12.14 ± 1.67 |
| 10 | CPH-8 | 26.79 ± 3.05 | 56.74 ± 3.26 | 12.05 ± 0.79 |
| 11 | CPH-9 | 8.05 ± 2.15 | 32.11 ± 0.50 | 22.72 ± 2.32 |
| 12 | CPH-10 | 46.97 ± 3.33 | 61.96 ± 2.23 | 14.54 ± 0.97 |
| 13 | CPH-11 | 43.18 ± 4.14 | 60.70 ± 3.04 | 15.06 ± 0.99 |

Examples 14-17

Evaluation of the Cytotoxicity of Metallocene Compounds CPH-12, CPH-13, CPH-14, and CPH-15 in Various Tumor Cell Lines Drug solutions of CPH-12, CPH-13, CPH-14, and CPH-15 were prepared and tested using substantially the same procedure as described in Examples 1-5. Table III summarizes the cytotoxicity test results of these metallocene compounds against the tumor cell lines A253 (head and neck tumor), A549 (lung carcinoma) and A2780 (ovarian cancer).

As illustrated in Table III, each of the metallocene compounds was active against the various cancer cell lines. Of these compounds, CPH-12 performed the best against all of the studied cancer lines, with average $IC_{50}$ values ranging from about 16 to about 31 μM. Generally, however, the results in Table III indicate that CPH-12, CPH-13, CPH-14, and CPH-15 were not as cytotoxic as several of the compounds listed in Table II (e.g., CPH-5 and CPH-7).

TABLE III

Comparison of $IC_{50}$ of Examples 14-17 for A253, A549, and A2780.

| | | $IC_{50}$ ± SD (μM) | | |
|---|---|---|---|---|
| Example | Compound | A253 | A549 | A2780 |
| 14 | CPH-12 | 29.73 ± 1.18 | 30.71 ± 0.26 | 16.88 ± 0.53 |
| 15 | CPH-13 | 38.95 ± 2.80 | 46.56 ± 0.92 | 22.56 ± 1.36 |
| 16 | CPH-14 | 30.70 ± 1.01 | 44.26 ± 4.36 | 33.20 ± 0.69 |
| 17 | CPH-15 | 106.62 ± 3.85 | 96.24 ± 1.23 | 24.09 ± 0.83 |

Examples 18-22

Evaluation of the Cytotoxicity of Metallocene Compounds CPH-1, CPH-2, and CPH-4 in A549 Lung Carcinoma Cell Line Examples 18-22 were prepared and tested as follows. Approximately 5,000 A549 cells (University of Texas M. D. Anderson Cancer Center) growing in RPMI 1640 were plated in each 96-well overnight before adding the test compounds for 96 hr of treatment. Final concentrations achieved in the wells were 0, 0.8, 1.6, 3.1, 6.2, 12.5, 25, 50, 100, and 200 μM. All of the test compounds were reconstituted in DMSO just before the treatment. The final concentration of DMSO solvent did not exceed 0.5 wt. %. After 96 hr, the medium was refreshed. Approximately 10 μL, of CellTiter-Blue® (Promega) was added to 100 μL of medium in each well and incubated at 37° C. for >4 hours. The plates were scanned using a SpectraMax M2 model microplate reader to measure the absorbance. CellTiter-Blue contains dark blue resazurin. Viable cells are able to convert non-fluorescent resazurin to its fluorescent product, resorufin. Nonviable cells are unable to reduce resazurin and thus do not display a fluorescent signal. Reduction of resazurin to resorufin also involves a shift of the absorbance maximum from 605 nm to 573 nm, so viability can also be estimated using absorbance. Results were normalized to untreated controls to determine the percent reduction in viability. Graphs were generated using GraphPad Prism (GraphPad Software, Inc).

Table IV summarizes the cytotoxicity test results of compounds CPH-1 (Example 18), CPH-2 (Example 19), and CPH-4 (Example 20) against the tumor cell line A549 (lung carcinoma). Results for Comparative Example 21 (titanocene=bis cyclopentadienyl titanium dichloride) and Comparative Example 22 (cisplatin) also are included in Table IV. In Table IV, the $IC_{50}$ values for CPH-1 and titanocene are listed as >200, indicating either a minor response (CPH-1) or no response (titanocene) against the A549 cell line, e.g., virtually no impact on cellular viability up to 200 μM. Interestingly, compounds CPH-2 and CPH-4 were active against the A549 cancer cell line, and surprisingly, with cytotoxicity similar to that of cisplatin under these testing conditions.

TABLE IV

Comparison of $IC_{50}$ of Examples 18-22 for A549.

| Example | Compound | $IC_{50}$ (μM) A549 |
|---|---|---|
| 18 | CPH-1 | >200 |
| 19 | CPH-2 | 75.2 |
| 20 | CPH-4 | 77.4 |
| 21 | Titanocene | >200 |
| 22 | Cisplatin | 82.7 |

Examples 23-27

Evaluation of the Cytotoxicity of Metallocene Compounds CPH-1, CPH-2, and CPH-4 in A2780 Ovarian Cancer Cell Line Examples 23-27 were prepared and tested using substantially the same procedure as described in Examples 18-22, except that approximately 2,000 A2780 ovarian cancer cells (University of Texas M. D. Anderson Cancer Center) were used. Table V summarizes the cytotoxicity test results of compounds CPH-1 (Example 23), CPH-2 (Example 24), and CPH-4 (Example 25) against the tumor cell line A2780 (ovarian cancer). Results for Comparative Example 26 (titanocene=bis cyclopentadienyl titanium dichloride) and Comparative Example 27 (cisplatin) also are included in Table V.

As illustrated in Table V, compounds CPH-2 and CPH-4 had surprisingly high activity against the A2780 cancer cell line, each with $IC_{50}$ values of about 21 μM or less, and with cytotoxic activity superior to cisplatin under these test conditions. The results for CPH-2 and CPH-4 (Examples 24-25) are relatively similar to those for CPH-2 and CPH-4 in Examples 2 and 6, respectively, against the A2780 ovarian cancer cell line.

TABLE V

Comparison of $IC_{50}$ of Examples 23-27 for A2780.

| Example | Compound | $IC_{50}$ (μM) A2780 |
|---|---|---|
| 23 | CPH-1 | >200 |
| 24 | CPH-2 | 21.0 |
| 25 | CPH-4 | 17.7 |
| 26 | Titanocene | 18.8 |
| 27 | Cisplatin | 35.4 |

Examples 28-33

Evaluation of the Cytotoxicity of Metallocene Compounds CPH-2, CPH-4, CPH-5, CPH-7, CPH-8, and CPH-9 in A2780 Ovarian Cancer Cell Line Examples 28-33 were prepared and tested using substantially the same procedure as described in Examples 18-22, except that approximately 5,000 A2780 ovarian cancer cells (University of Texas M. D. Anderson Cancer Center) were used. Table VI summarizes the cytotoxicity test results of compounds CPH-2, CPH-4, CPH-5, CPH-7, CPH-8, and CPH-9 against the A2780 ovarian cancer cell line.

Unexpectedly, each of these compounds showed remarkably high activity against the A2780 cancer cell line, each with $IC_{50}$ values of less than 19 μM, as illustrated in Table VI. These results (Examples 28-33) are relatively consistent with the test results against the A2780 cancer cell line shown in Examples 2, 6-7, 9-11, and 24-25.

TABLE VI

Comparison of $IC_{50}$ of Examples 28-33 for A2780.

| Example | Compound | $IC_{50}$ (μM) A2780 |
|---|---|---|
| 28 | CPH-2 | 17.7 |
| 29 | CPH-4 | 7.5 |
| 30 | CPH-5 | 18.6 |
| 31 | CPH-7 | 17.7 |
| 32 | CPH-8 | 8.6 |
| 33 | CPH-9 | 15.6 |

Examples 34-37

Evaluation of the Cytotoxicity of Metallocene Compounds CPH-4, CPH-5, and CPH-9 Against SKOV-3 Chemoresistant Ovarian Cancer Cells Examples 34-37 were prepared and tested using substantially the same procedure as described in Examples 18-22, except that approximately 5,000 SKOV-3 ovarian cancer cells (American Type Culture Collection) were used. Table VII summarizes the cytotoxicity test results of compounds CPH-4, CPH-5, and CPH-9 against SKOV-3 chemoresistant ovarian cancer cells, as well as for Comparative Example 37 (cisplatin).

Unexpectedly, CPH-4, CPH-5, and CPH-9 showed remarkably high activity against the SKOV-3 cancer cells, comparable to or better than cisplatin. Surprisingly, CPH-5 provided an order of magnitude improvement in cytotoxic activity.

TABLE VII

Comparison of $IC_{50}$ of Examples 34-37 for SKOV-3.

| Example | Compound | $IC_{50}$ (μM) SKOV-3 |
|---|---|---|
| 34 | CPH-4 | 8.1 |
| 35 | CPH-5 | <1 |
| 36 | CPH-9 | 14.4 |
| 37 | Cisplatin | 12.8 |

Examples 38-41

Evaluation of the Cytotoxicity of Metallocene Compounds CPH-4, CPH-5, and CPH-9 Against Hey-A8 MDR Chemoresistant Ovarian Cancer Cells Examples 38-41 were prepared and tested using substantially the same procedure as described in Examples 18-22, except that approximately 5,000 Hey-A8 MDR ovarian cancer cells (University of Texas M. D. Anderson Cancer Center) were used. Table VIII summarizes the cytotoxicity test results of compounds CPH-4, CPH-5, and CPH-9 against Hey-A8 MDR chemoresitant ovarian cancer cells, as well as for Comparative Example 41 (paclitaxel). While apparently not as potent as Example 41, each of CPH-4, CPH-5, and CPH-9 demonstrated surprising cytotoxic activity against the Hey-A8 MDR cancer cells, with CPH-9 being the most cytotoxic of the metallocene compounds.

TABLE VIII

Comparison of $IC_{50}$ of Examples 38-41 for Hey-A8 MDR cells.

| Example | Compound | $IC_{50}$ (μM) Hey-A8 MDR |
|---|---|---|
| 38 | CPH-4 | 21.2 |
| 39 | CPH-5 | 26.9 |
| 40 | CPH-9 | 1.1 |
| 41 | Paclitaxel | 0.03 |

Examples 42-45

Evaluation of the Cytotoxicity of Metallocene Compounds CPH-4, CPH-5, and CPH-9 Against NCI-Adr-Res Chemoresistant Ovarian Cancer Cells Examples 42-45 were prepared and tested using substantially the same procedure as described in Examples 18-22, except that approximately 5,000 NCI-Adr-Res ovarian cancer cells (National Cancer Institute) were used. Table IX summarizes the cytotoxicity test results of compounds CPH-4, CPH-5, and CPH-9 against NCI-Adr-Res chemoresitant ovarian cancer cells, as well as for Comparative Example 41 (doxorubicin). At concentrations up to about 200 μM, the metallocene compounds appeared to have virtually no impact on cellular viability.

TABLE IX

Comparison of $IC_{50}$ of Examples 42-45 for NCI-Adr-Res cells.

| Example | Compound | $IC_{50}$ (μM) NCI-Adr-Res |
|---|---|---|
| 42 | CPH-4 | 178.1 |
| 43 | CPH-5 | >200 |
| 44 | CPH-9 | >200 |
| 45 | Doxorubicin | 14.3 |

Examples 46-49

Evaluation of the Cytotoxicity of Metallocene Compounds CPH-4, CPH-5, and CPH-9 Against T-24 Chemoresistant Urinary Bladder Cancer Cells Examples 46-49 were prepared and tested using substantially the same procedure as described in Examples 18-22, except that approximately 5,000 T-24 urinary bladder cancer cells (American Type Culture Collection) were used. Table X summarizes the cytotoxicity test results of compounds CPH-4, CPH-5, and CPH-9 against T-24 chemoresitant cancer cells, as well as for Comparative Example 49 (cisplatin).

Unexpectedly, CPH-4, CPH-5, and CPH-9 showed remarkably high activity against the T-24 cancer cells, far superior to that of cisplatin.

TABLE X

Comparison of IC$_{50}$ of Examples 46-49 for T-24 cells.

| Example | Compound | IC$_{50}$ (μM) T-24 |
|---|---|---|
| 46 | CPH-4 | 27.3 |
| 47 | CPH-5 | 28.3 |
| 48 | CPH-9 | 15.1 |
| 49 | Cisplatin | >200 |

Examples 50-53

Evaluation of the Cytotoxicity of Metallocene Compounds CPH-4, CPH-5, and CPH-9 Against MeWo Chemoresistant Melanoma Cancer Cells Examples 50-53 were prepared and tested using substantially the same procedure as described in Examples 18-22, except that approximately 5,000 MeWo melanoma cancer cells (University of Texas M. D. Anderson Cancer Center) were used. Table XI summarizes the cytotoxicity test results of compounds CPH-4, CPH-5, and CPH-9 against the MeWo melanoma cancer cells, as well as for Comparative Example 53 (dacarbazine).

Unexpectedly, CPH-4, CPH-5, and CPH-9 showed remarkably high activity against the melanoma cancer cells, comparable to or better than dacarbazine. Surprisingly, CPH-9 provided a significant improvement in cytotoxic activity.

TABLE XI

Comparison of IC$_{50}$ of Examples 50-53 for MeWo melanoma cancer cells.

| Example | Compound | IC$_{50}$ (μM) MeWo melanoma |
|---|---|---|
| 50 | CPH-4 | 6.9 |
| 51 | CPH-5 | 6.1 |
| 52 | CPH-9 | 1.6 |
| 53 | Dacarbazine | 7.9 |

The invention has been described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following:

Embodiment 1

A method of treating cancer in a subject in need thereof, comprising administering to the subject a composition comprising:

a therapeutically effective amount of a metallocene compound having formula MET-A, or a pharmaceutically acceptable salt thereof:

$$E_p(Cp^A R^A{}_m)(Cp^B R^B{}_n)MX^1 X^2 \quad \text{(MET-A); and}$$

optionally a pharmaceutically acceptable diluent, excipient, or carrier; wherein:

M is Ti, Zr, or Hf;
$Cp^A$ is a cyclopentadienyl, indenyl, or fluorenyl group; $Cp^B$ is an indenyl or fluorenyl group;

each $R^A$ and $R^B$ independently is H, a halide, hydrocarbyl group, halogenated hydrocarbyl group, oxygen-containing group, sulfur-containing group, nitrogen-containing group, or silicon-containing group;
E is a bridging group selected from:
a bridging group having the formula $>E^{3A}R^{7A}R^{8A}$, wherein $E^{3A}$ is C or Si, and $R^{7A}$ and $R^{8A}$ are independently H or a hydrocarbyl group, halogenated hydrocarbyl group, oxygen-containing group, sulfur-containing group, nitrogen-containing group, or silicon-containing group;
a bridging group having the formula —$CR^{7B}R^{8B}$—$CR^{7C}R^{8C}$—, wherein $R^{7B}$, $R^{8B}$, $R^{7C}$, and $R^{8C}$ are independently H or a $C_1$ to $C_{18}$ hydrocarbyl group, or
a bridging group having the formula —$SiR^{7D}SiR^{8D}$—$SiR^{7E}R^{8E}$—, wherein $R^{7D}$, $R^{8D}$, $R^{7E}$, and $R^{8E}$ are independently H or a $C_1$ to $C_{18}$ hydrocarbyl group;
$X^1$ and $X^2$ independently are monoanionic ligands;
m is 0, 1, 2, 3, 4, or 5;
n is 0, 1, 2, 3, 4, or 5; and
p is 0 or 1.

Embodiment 2

A method of treating cancer in a subject in need thereof, comprising administering to the subject a composition comprising:

a therapeutically effective amount of a metallocene compound having formula MET-A, or a pharmaceutically acceptable salt thereof:

$$E_p(Cp^A R^A{}_m)(Cp^B R^B{}_n)MX^1 X^2 \quad \text{(MET-A); and}$$

optionally a pharmaceutically acceptable diluent, excipient, or carrier; in combination with a therapeutically effective amount of any therapeutic agent disclosed herein; wherein:

M is Ti, Zr, or Hf;
$Cp^A$ is a cyclopentadienyl, indenyl, or fluorenyl group;
$Cp^B$ is an indenyl or fluorenyl group;
each $R^A$ and $R^B$ independently is H, a halide, hydrocarbyl group, halogenated hydrocarbyl group, oxygen-containing group, sulfur-containing group, nitrogen-containing group, or silicon-containing group;
E is a bridging group selected from:
a bridging group having the formula $>E^{3A}R^{7A}R^{8A}$, wherein $E^{3A}$ is C or Si, and $R^{7A}$ and $R^{8A}$ are independently H or a hydrocarbyl group, halogenated hydrocarbyl group, oxygen-containing group, sulfur-containing group, nitrogen-containing group, or silicon-containing group;
a bridging group having the formula —$CR^{7B}R^{8B}$—$CR^{7C}R^{8C}$—, wherein $R^{7B}$, $R^{8B}$, $R^{7C}$, and $R^{8C}$ are independently H or a $C_1$ to $C_{18}$ hydrocarbyl group, or
a bridging group having the formula —$SiR^{7D}R^{8D}$—$SiR^{7E}R^{8E}$—, wherein $R^{7D}$, $R^{8D}$, $R^{7E}$, and $R^{8E}$ are independently H or a $C_1$ to $C_{18}$ hydrocarbyl group;
$X^1$ and $X^2$ independently are monoanionic ligands;
m is 0, 1, 2, 3, 4, or 5;
n is 0, 1, 2, 3, 4, or 5; and
p is 0 or 1.

Embodiment 3

The method defined in embodiment 2, wherein the therapeutic agent comprises methotrexate, pemetrexed, cladribine, clofarabine, fludarabine, 6-mercaptopurine, nelarabine, pentostatin, capecitabine, cytarabine, 5-fluorouracil, gemcitabine, hydroxyurea, interferon, bleomycin, carmustine, lomustine, bendamustine, chlorambucil, cyclophosphamide, ifosfamide, mechlorethamine, melphalan, dacarbazine, temozolomide, procarbazine, asparaginase, bicalutamide, flutamide, fulvestrant, leuprolide acetate, megestrol acetate, tamoxifen, anastrozole, exemestane, letrozole, alemtuzumab, bevacizumab, gemtuzumab, ibritumomab tiuxetan, iodine-131 tositumomab, tositumomab, rituximab, trastuzumab, mitomycin, carboplatin, cisplatin, oxaliplatin, bortezomib, docetaxel, paclitaxel, vinblastine, vincristine, vinorelbine, daunorubicin, doxorubicin, epirubicin, irinotecan, topotecan, etoposide, teniposide, mitoxantrone, erlotinib, gefitinib, imatinib, lapatinib, sorafenib, sunitinib, or a mixture thereof.

Embodiment 4

The method defined in embodiment 2, wherein the therapeutic agent comprises alemtuzumab, aminoglutethimide, anastrozole, asparginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, vorinostat, or a mixture thereof.

Embodiment 5

The method defined in embodiment 2, wherein the therapeutic agent comprises bevacizumab, dacarbazine, docetaxel, 5-fluorouracil, gemcitabine, ipilimumab, paclitaxel, or a mixture thereof.

Embodiment 6

The method defined in embodiment 2, wherein the therapeutic agent comprises dacarbazine, paclitaxel, doxorubicin, or a mixture thereof.

Embodiment 7

The method defined in any one of embodiments 2 to 6, wherein the therapeutically effective amount of the metallocene compound administered in combination with the therapeutically effective amount of the therapeutic agent results in a synergistic increase in cytotoxicity.

Embodiment 8

Use of a metallocene compound having formula MET-A, or a pharmaceutically acceptable salt thereof, in the manufacture of a medicament for the treatment of cancer in a subject in need thereof:

$$E_p(Cp^A R^A{}_m)(Cp^B R^B{}_n)MX^1 X^2 \quad \text{(MET-A);}$$

wherein:
M is Ti, Zr, or Hf;
$Cp^A$ is a cyclopentadienyl, indenyl, or fluorenyl group;
$Cp^B$ is an indenyl or fluorenyl group;
each $R^A$ and $R^B$ independently is H, a halide, hydrocarbyl group, halogenated hydrocarbyl group, oxygen-containing group, sulfur-containing group, nitrogen-containing group, or silicon-containing group;
E is a bridging group selected from:
  a bridging group having the formula $>E^{3A}R^{7A}R^{8A}$, wherein $E^{3A}$ is C or Si, and $R^{7A}$ and $R^{8A}$ are independently H or a hydrocarbyl group, halogenated hydrocarbyl group, oxygen-containing group, sulfur-containing group, nitrogen-containing group, or silicon-containing group;
  a bridging group having the formula $-CR^{7B}R^{8B}CR^{2C}R^{8C}-$ wherein $R^{7B}$, $R^{8B}$, $R^{7C}$, and $R^{8C}$ are independently H or a $C_1$ to $C_{18}$ hydrocarbyl group, or
  a bridging group having the formula $-SiR^{7D}R^{8D}-SiR^{7E}R^{8E}-$, wherein $R^{7C}$, $R^{8D}$, $R^{7E}$, and $R^{8E}$ are independently H or a $C_1$ to $C_{18}$ hydrocarbyl group;
$X^1$ and $X^2$ independently are monoanionic ligands;
m is 0, 1, 2, 3, 4, or 5;
n is 0, 1, 2, 3, 4, or 5; and
p is 0 or 1.

Embodiment 9

The method or use defined in any one of embodiments 1 to 8, wherein the cancer is any cancer disclosed herein, for example, brain, lung, liver, spleen, kidney, lymph node, small intestine, pancreatic, blood cell, bone, colon, stomach, urinary bladder, gall bladder, breast, endometrium, renal, prostate, testicular, ovarian, cervical, central nervous system, skin, head and neck, esophageal, or bone marrow cancer.

Embodiment 10

The method or use defined in any one of embodiments 1 to 8, wherein the cancer is ovarian cancer.

Embodiment 11

The method or use defined in any one of embodiments 1 to 8, wherein the cancer is testicular cancer.

Embodiment 12

The method or use defined in any one of embodiments 1 to 8, wherein the cancer is head and neck cancer.

Embodiment 13

The method or use defined in any one of embodiments 1 to 8, wherein the cancer is esophageal cancer.

Embodiment 14

The method or use defined in any one of embodiments 1 to 8, wherein the cancer is urinary bladder cancer.

Embodiment 15

The method or use defined in any one of embodiments 1 to 8, wherein the cancer is stomach cancer.

Embodiment 16

The method or use defined in any one of embodiments 1 to 8, wherein the cancer is lung cancer.

Embodiment 17

The method or use defined in any one of embodiments 1 to 8, wherein the cancer is small cell lung cancer.

Embodiment 18

The method or use defined in any one of embodiments 1 to 8, wherein the cancer is non-small cell lung cancer.

Embodiment 19

The method or use defined in any one of embodiments 1 to 8, wherein the cancer is leukemia, lymphoma, or melanoma.

Embodiment 20

The method or use defined in any one of embodiments 1 to 8, wherein the cancer is non-Hodgkin lymphoma.

Embodiment 21

The method or use defined in any one of embodiments 1 to 8, wherein the cancer is melanoma.

Embodiment 22

The method or use defined in any one of embodiments 1 to 21, wherein the cancer is resistant or insensitive to treatment with one or more of the following therapeutic agents: methotrexate, pemetrexed, cladribine, clofarabine, fludarabine, 6-mercaptopurine, nelarabine, pentostatin, capecitabine, cytarabine, 5-fluorouracil, gemcitabine, hydroxyurea, interferon, bleomycin, carmustine, lomustine, bendamustine, chlorambucil, cyclophosphamide, ifosfamide, mechlorethamine, melphalan, dacarbazine, temozolomide, procarbazine, asparaginase, bicalutamide, flutamide, fulvestrant, leuprolide acetate, megestrol acetate, tamoxifen, anastrozole, exemestane, letrozole, alemtuzumab, bevacizumab, gemtuzumab, ibritumomab tiuxetan, iodine-131 tositumomab, tositumomab, rituximab, trastuzumab, mitomycin, carboplatin, cisplatin, oxaliplatin, bortezomib, docetaxel, paclitaxel, vinblastine, vincristine, vinorelbine, daunorubicin, doxorubicin, epirubicin, irinotecan, topotecan, etoposide, teniposide, mitoxantrone, erlotinib, gefitinib, imatinib, lapatinib, sorafenib, and/or sunitinib.

Embodiment 23

The method or use defined in any one of embodiments 1 to 21, wherein the cancer is resistant or insensitive to treatment with one or more of the following therapeutic agents: alemtuzumab, aminoglutethimide, anastrozole, asparginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, and/or vorinostat.

Embodiment 24

The method or use defined in any one of embodiments 1 to 21, wherein the cancer is resistant or insensitive to treatment with a platinum agent.

Embodiment 25

The method or use defined in any one of embodiments 1 to 21, wherein the cancer is resistant or insensitive to treatment with a taxane.

Embodiment 26

The method or use defined in any one of embodiments 1 to 21, wherein the cancer is resistant or insensitive to treatment with dacarbazine.

Embodiment 27

The method or use defined in any one of embodiments 1 to 8, wherein the cancer is SKOV-3 ovarian cancer.

Embodiment 28

The method or use defined in any one of embodiments 1 to 8, wherein the cancer is Hey-A8 MDR ovarian cancer.

Embodiment 29

The method or use defined in any one of embodiments 1 to 8, wherein the cancer is T-24 urinary bladder cancer.

Embodiment 30

The method or use defined in any one of embodiments 1 to 8, wherein the cancer is MeWo melanoma.

Embodiment 31

A method of inhibiting or reducing tumor growth in a subject in need thereof, comprising administering to the subject a composition comprising:

a therapeutically effective amount of a metallocene compound having formula MET-A, or a pharmaceutically acceptable salt thereof:

$$E_p(Cp^A R^A_m)(Cp^B R^B_n)MX^1 X^2 \quad \text{(MET-A); and}$$

optionally a pharmaceutically acceptable diluent, excipient, or carrier;
wherein the growth of the tumor is inhibited or reduced;
wherein:
M is Ti, Zr, or Hf;
$Cp^A$ is a cyclopentadienyl, indenyl, or fluorenyl group;
$Cp^B$ is an indenyl or fluorenyl group;

each $R^A$ and $R^B$ independently is H, a halide, hydrocarbyl group, halogenated hydrocarbyl group, oxygen-containing group, sulfur-containing group, nitrogen-containing group, or silicon-containing group;

E is a bridging group selected from:
a bridging group having the formula $>E^{3A}R^{7A}R^{8A}$, wherein $E^{3A}$ is C or Si, and $R^{7A}$ and $R^{8A}$ are independently H or a hydrocarbyl group, halogenated hydrocarbyl group, oxygen-containing group, sulfur-containing group, nitrogen-containing group, or silicon-containing group;
a bridging group having the formula $—CR^{2B}R^{8B}—CR^{2C}R^{8C}—$, wherein $R^{7B}$, $R^{8B}$, $R^{7C}$, and $R^{8C}$ are independently H or a $C_1$ to $C_{18}$ hydrocarbyl group, or
a bridging group having the formula $—SiR^{7D}R^{8D}—SiR^{7E}R^{8E}—$, wherein $R^{7D}$, $R^{8D}$, $R^{7E}$, and $R^{8E}$ are independently H or a $C_1$ to $C_{18}$ hydrocarbyl group;

$X^1$ and $X^2$ independently are monoanionic ligands;
m is 0, 1, 2, 3, 4, or 5;
n is 0, 1, 2, 3, 4, or 5; and
p is 0 or 1.

Embodiment 32

The method or use defined in any one of the preceding embodiments, wherein the subject is a mammal Embodiment 33

The method or use defined in any one of the preceding embodiments, wherein the subject is a human.

Embodiment 34

The method or use defined in any one of the preceding embodiments, wherein the composition or medicament is administered orally, parenterally, topically, or transmucosally.

Embodiment 35

The method or use defined in any one of the preceding embodiments, wherein the composition or medicament is administered subcutaneously, intramuscularly, or intravenously.

Embodiment 36

The method or use defined in any one of the preceding embodiments, wherein the therapeutically effective amount of the metallocene compound is in a range from about 0.001 mg/kg to about 1000 mg/kg.

Embodiment 37

The method or use defined in any one of the preceding embodiments, wherein the therapeutically effective amount of the metallocene compound is in a range from about 0.1 mg/kg to about 10 mg/kg.

Embodiment 38

The method or use defined in any one of the preceding embodiments, wherein the method or use results in an increase in progression-free survival (PFS) of between 1 month and about 24 months.

Embodiment 39

The method or use defined in any one of the preceding embodiments, wherein the method or use results in an increase in overall survival (OS) of between about 2 months and about 48 months.

Embodiment 40

The method or use defined in any one of the preceding embodiments, wherein the method or use results in an increase in an overall response rate (RR) in a range from about 10% to about 75%.

Embodiment 41

A pharmaceutical composition comprising:
a therapeutically effective amount of a metallocene compound having formula MET-A, or a pharmaceutically acceptable salt thereof:

$$E_p(Cp^A R^A{}_m)(Cp^B R^B{}_n)MX^1X^2 \quad \text{(MET-A); and}$$

a pharmaceutically acceptable diluent, excipient, or carrier; wherein:

M is Ti, Zr, or Hf;
$Cp^A$ is a cyclopentadienyl, indenyl, or fluorenyl group;
$Cp^B$ is an indenyl or fluorenyl group;
each $R^A$ and $R^B$ independently is H, a halide, hydrocarbyl group, halogenated hydrocarbyl group, oxygen-containing group, sulfur-containing group, nitrogen-containing group, or silicon-containing group;

E is a bridging group selected from:
a bridging group having the formula $>E^{3A}R^{7A}R^{8A}$, wherein $E^{3A}$ is C or Si, and $R^{7A}$ and $R^{8A}$ are independently H or a hydrocarbyl group, halogenated hydrocarbyl group, oxygen-containing group, sulfur-containing group, nitrogen-containing group, or silicon-containing group;
a bridging group having the formula $—CR^{2B}R^{8B}—CR^{2C}R^{8C}—$, wherein $R^{7B}$, $R^{8B}$, $R^{7C}$, and $R^{8C}$ are independently H or a $C_1$ to $C_{18}$ hydrocarbyl group, or
a bridging group having the formula $—SiR^{2D}R^{8D}—SiR^{7E}R^{8E}—$, wherein $R^{7D}$, $R^{8D}$, $R^{7E}$, and $R^{8E}$ are independently H or a $C_1$ to $C_{18}$ hydrocarbyl group;

$X^1$ and $X^2$ independently are monoanionic ligands;
m is 0, 1, 2, 3, 4, or 5;
n is 0, 1, 2, 3, 4, or 5; and
p is 0 or 1.

Embodiment 42

The composition defined in embodiment 41, wherein the composition is a composition for treating cancer in a subject in need thereof.

Embodiment 43

The composition defined in embodiment 41, wherein the composition is a composition for inhibiting or reducing tumor growth in a subject in need thereof.

Embodiment 44

The composition defined in any one of embodiments 41 to 43, wherein a weight percent of the metallocene compound in the pharmaceutical composition is in a range from about 0.1% to about 99%.

Embodiment 45

The composition defined in any one of embodiments 41 to 44, wherein a weight percent of the metallocene compound in the pharmaceutical composition is in a range from about 1% to about 25%.

Embodiment 46

The composition defined in any one of embodiments 41 to 45, wherein the composition is in the form of a solution, suspension, tablet, capsule, pill, lozenge, powder, or granule.

Embodiment 47

The composition defined in any one of embodiments 41 to 45, wherein the composition is in the form of a cream, ointment, patch, spray, or inhalant.

Embodiment 48

The composition defined in any one of embodiments 41 to 45, wherein the composition is formulated for oral, parenteral, topical, or transmucosal administration.

Embodiment 49

The composition defined in any one of embodiments 41 to 45, wherein the composition is formulated for subcutaneous, intramuscular, or intravenous administration.

Embodiment 50

The composition defined in any one of embodiments 41 to 49, wherein the composition is a cancer-treating composition characterized by an $IC_{50}$ ($\mu M$) of less than 50.

Embodiment 51

The composition defined in any one of embodiments 41 to 50, wherein the composition is a cancer-treating composition characterized by an $IC_{50}$ ($\mu M$) of less than 25.

Embodiment 52

The composition defined in any one of embodiments 41 to 51, wherein the composition is a cancer-treating composition characterized by an $IC_{50}$ ($\mu M$) of less than 10.

Embodiment 53

The composition defined in any one of embodiments 41 to 52, wherein the composition is capable of killing 50% of cancer cells in 96 hours.

Embodiment 54

The method, use, or composition defined in any one of embodiments 1-53, wherein $Cp^A$ is a cyclopentadienyl group and $Cp^B$ is an indenyl group.

Embodiment 55

The method, use, or composition defined in any one of embodiments 1-53, wherein $Cp^A$ is a cyclopentadienyl group and $Cp^B$ is a fluorenyl group.

Embodiment 56

The method, use, or composition defined in any one of embodiments 1-53, wherein $Cp^A$ is an indenyl group and $Cp^B$ is an indenyl group.

Embodiment 57

The method, use, or composition defined in any one of embodiments 1-53, wherein $Cp^A$ is an indenyl group and $Cp^B$ is a fluorenyl group.

Embodiment 58

The method, use, or composition defined in any one of embodiments 1-53, wherein $Cp^A$ is a fluorenyl group and $Cp^B$ is a fluorenyl group.

Embodiment 59

The method, use, or composition defined in any one of embodiments 1-58, wherein each $R^A$ and/or $R^B$ independently is H or any halide, hydrocarbyl group, halogenated hydrocarbyl group, oxygen-containing group, sulfur-containing group, nitrogen-containing group, or silicon-containing group disclosed herein.

Embodiment 60

The method, use, or composition defined in any one of embodiments 1-59, wherein at least one $R^A$ and/or $R^B$ independently is any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 61

The method, use, or composition defined in any one of embodiments 1-59, wherein at least one $R^A$ and/or $R^B$ independently is a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group.

Embodiment 62

The method, use, or composition defined in any one of embodiments 1-59, wherein at least one $R^A$ and/or $R^B$ independently is any $C_1$ to $C_{18}$ halogenated hydrocarbyl group disclosed herein, for example, pentafluorophenyl, trifluoromethyl, etc.

Embodiment 63

The method, use, or composition defined in any one of embodiments 1-59, wherein at least one $R^A$ and/or $R^B$ independently is any oxygen-containing group having up to 18 carbon atoms disclosed herein, for example, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a nitro-phenoxy group, a tert-pentoxy group, a 3-methyl-1- butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), an acetate group, a trichloroacetate group, a hydrogen maleinate group, a polyol group, a polyethylene glycol (PEG) group, —OBR$^C_2$, —OSO$_2$R$^C$, —OCOCH$_2$NR$^C_3$X, or —OCOCH(R$^C$)NR$^C_3$X, etc., wherein each X independently is any halide disclosed herein and each R$^C$ independently is H or any C$_1$ to C$_{18}$ hydrocarbyl group disclosed herein, for example, any C$_1$ to C$_{10}$ alkyl group, C$_2$ to C$_{10}$ alkenyl group, C$_4$ to C$_{10}$ cycloalkyl group, C$_6$ to C$_{10}$ aryl group, or C$_7$ to C$_{10}$ aralkyl group disclosed herein.

Embodiment 64

The method, use, or composition defined in any one of embodiments 1-59, wherein at least one R$^A$ and/or R$^B$ independently has the formula —R$^D$OR$^D$ or —R$^D$(CO)OR$^D$, wherein each R$^D$ independently is H or any hydrocarbyl group, halogenated hydrocarbyl group, oxygen-containing group, sulfur-containing group, nitrogen-containing group, or silicon-containing group disclosed herein.

Embodiment 65

The method, use, or composition defined in any one of embodiments 1-59, wherein at least one R$^A$ and/or R$^B$ independently is any sulfur-containing group having up to 18 carbon atoms disclosed herein, for example, a C$_1$ to C$_{18}$ thiocarboxy group, a methylthiolate group, an ethylthiolate group, a phenylthiolate group, an alkylammonium chloride phenylthiolate group, etc.

Embodiment 66

The method, use, or composition defined in any one of embodiments 1-59, wherein at least one R$^A$ and/or R$^B$ independently is any nitrogen-containing group having up to 18 carbon atoms disclosed herein, for example, a C$_1$ to C$_{18}$ hydrocarbylaminyl group, a methylaminyl group, an ethylaminyl group, a propylaminyl group, a phenylaminyl group, a dimethylaminyl group, a di-ethylaminyl group, a di-propylaminyl group, a di-phenylaminyl group, —N(SiMe$_3$)$_2$, —N(SiEt$_3$)$_2$, —N=C=S, an ammonium group (—NR$^C_3$X), etc., wherein X is a any halide disclosed herein and each R$^C$ independently is H or a C$_1$ to C$_{18}$ hydrocarbyl group, for example, any C$_1$ to C$_{10}$ alkyl group, C$_2$ to C$_{10}$ alkenyl group, C$_4$ to C$_{10}$ cycloalkyl group, C$_6$ to C$_{10}$ aryl group, or C$_7$ to C$_{10}$ aralkyl group disclosed herein.

Embodiment 67

The method, use, or composition defined in any one of embodiments 1-59, wherein at least one R$^A$ and/or R$^B$ independently is any silicon-containing group having up to 18 carbon atoms disclosed herein, for example, any C$_1$ to C$_{18}$ hydrocarbylsilyl group disclosed herein, such as trimethylsilyl, triethylsilyl, tripropylsilyl, tributylsilyl, tripentylsilyl, triphenylsilyl, allyldimethylsilyl, etc.

Embodiment 68

The method, use, or composition defined in any one of the preceding embodiments, wherein m is 0, 1, or 2.

Embodiment 69

The method, use, or composition defined in any one of the preceding embodiments, wherein n is 0, 1, or 2.

Embodiment 70

The method, use, or composition defined in any one of the preceding embodiments, wherein m or n is equal to 0.

Embodiment 71

The method, use, or composition defined in any one of the preceding embodiments, wherein m and n are both equal to 0.

Embodiment 72

The method, use, or composition defined in any one of embodiments 1-71, wherein E is a bridging group having the formula >E$^{3A}$R$^{7A}$R$^{8A}$, and wherein E$^{3A}$ is C or Si, and R$^{7A}$ and R$^{8A}$ are independently H or any hydrocarbyl group, halogenated hydrocarbyl group, oxygen-containing group, sulfur-containing group, nitrogen-containing group, or silicon-containing group disclosed herein.

Embodiment 73

The method, use, or composition defined in any one of >E$^{3A}$R$^{7A}$R$^{8A}$, embodiments 1-72, wherein E is a bridging group having the formula and wherein E$^{3A}$ is C, and at least one of R$^{7A}$ and R$^{8A}$ is any C$_1$ to C$_{18}$ hydrocarbyl group disclosed herein, for example, any C$_1$ to C$_{10}$ alkyl group, C$_2$ to C$_{10}$ alkenyl group, C$_4$ to C$_{10}$ cycloalkyl group, C$_6$ to C$_{10}$ aryl group, or C$_7$ to C$_{10}$ aralkyl group disclosed herein.

Embodiment 74, The method, use, or composition defined in any one of embodiments 1-72, wherein E is a bridging group having the formula >E$^{3A}$R$^{7A}$R$^{8A}$, and wherein E$^{3A}$ is C, and at least one of R$^{7A}$ and R$^{8A}$ is a phenyl group.

Embodiment 75

The method, use, or composition defined in any one of >E$^{3A}$R$^{7A}$R$^{8A}$, embodiments 1-72, wherein E is a bridging group having the formula and wherein E$^{3A}$ is C, and at least one of R$^{7A}$ and R$^{8A}$ is a terminal alkenyl group having up to 6 carbon atoms.

Embodiment 76

The method, use, or composition defined in any one of embodiments 1-72, wherein E is a bridging group having the formula >E$^{3A}$R$^{7A}$R$^{8A}$, and wherein E$^{3A}$ is C, and R$^{7A}$ and R$^{8A}$ are independently methyl, ethyl, propyl, butyl, pentyl, hexyl, heptyl, octyl, ethenyl, propenyl, butenyl, pentenyl, hexenyl, heptenyl, octenyl, phenyl, tolyl, or benzyl.

Embodiment 77

The method, use, or composition defined in any one of >E$^{3A}$R$^{7A}$R$^{8A}$, embodiments 1-72, wherein E is a bridging group having the formula and wherein E$^{3A}$ is C, and both of R$^{7A}$ and R$^{8A}$ are phenyl groups.

Embodiment 78

The method, use, or composition defined in any one of embodiments 1-72, wherein E is a bridging group having the

Embodiment 79

The method, use, or composition defined in any one of embodiments 1-72, wherein E is a bridging group having the formula $>E^{3A}R^{7A}R^{8A}$, and wherein $E^{3A}$ is C, and at least one of $R^{7A}$ and $R^{8A}$ independently is any oxygen-containing group having up to 18 carbon atoms disclosed herein, for example, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a nitro-phenoxy group, a tert-pentoxy group, a 3-methyl-1-butoxy group, a 3-methyl-2-butoxy group, a neopentoxy group, a phenoxy group, a toloxy group, a xyloxy group, a 2,4,6-trimethylphenoxy group, a benzoxy group, an acetylacetonate group (acac), an acetate group, a trichloroacetate group, a hydrogen maleinate group, a polyol group, a polyethylene glycol (PEG) group, $-OBR^{C}_2$, $-OSO_2R^C$, $-OCOCH_2NR^C_3X$, or $-OCOCH(Rc)NR^C_3X$, etc., wherein each X independently is any halide disclosed herein and each $R^C$ independently is H or any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 80

The method, use, or composition defined in any one of embodiments 1-72, wherein E is a bridging group having the formula $>E^{3A}R^{7A}R^{8A}$, and wherein $E^{3A}$ is C, and at least one of $R^{7A}$ and $R^{8A}$ has the formula $-R^DOR^D$ or $-R^D(CO)OR^D$, wherein each $R^D$ independently is H or any hydrocarbyl group, halogenated hydrocarbyl group, oxygen-containing group, sulfur-containing group, nitrogen-containing group, or silicon-containing group disclosed herein.

Embodiment 81

The method, use, or composition defined in any one of $>E^{3A}R^{7A}R^{8A}$, embodiments 1-72, wherein E is a bridging group having the formula and wherein $E^{3A}$ is C, and at least one of $R^{7A}$ and $R^{8A}$ is any sulfur-containing group having up to 18 carbon atoms disclosed herein, for example, a $C_1$ to $C_{18}$ thiocarboxy group, a methylthiolate group, an ethylthiolate group, a phenylthiolate group, an alkylammonium chloride phenylthiolate group, etc.

Embodiment 82

The method, use, or composition defined in any one of embodiments 1-72, wherein E is a bridging group having the formula $>E^{3A}R^{7A}R^{8A}$, and wherein $E^{3A}$ is C, and at least one of $R^{7A}$ and $R^{8A}$ is any nitrogen-containing group having up to 18 carbon atoms disclosed herein, for example, a $C_1$ to $C_{18}$ hydrocarbylaminyl group, a methylaminyl group, an ethylaminyl group, a propylaminyl group, a phenylaminyl group, a dimethylaminyl group, a di-ethylaminyl group, a di-propylaminyl group, a di-phenylaminyl group, $-N(SiMe_3)_2$, $-N(SiEt_3)_2$, $-N=C=S$, an ammonium group ($-NR^C_3X$), etc., wherein X is a any halide disclosed herein and each $R^C$ independently is H or a $C_1$ to $C_{18}$ hydrocarbyl group, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 83

The method, use, or composition defined in any one of $>E^{3A}R^{7A}R^{8A}$, embodiments 1-72, wherein E is a bridging group having the formula and wherein $E^{3A}$ is C, and at least one of $R^{7A}$ and $R^{8A}$ is any silicon-containing group having up to 18 carbon atoms disclosed herein, for example, any $C_1$ to $C_{18}$ hydrocarbylsilyl group disclosed herein, such as trimethylsilyl, triethylsilyl, tripropylsilyl, tributylsilyl, tripentylsilyl, triphenylsilyl, allyldimethylsilyl, etc.

Embodiment 84

The method, use, or composition defined in any one of embodiments 1-71, wherein E is a bridging group having the formula $-CR^{7B}R^{8B}CR^{7C}R^{8C}$, and wherein $R^{7B}$, $R^{8B}$, $R^{7C}$, and $R^{8C}$ are independently H or any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 85

The method, use, or composition defined in any one of embodiments 1-71, wherein E is a bridging group having the formula $-CR^{7B}R^{8B}-CR^{7C}R^{8C}-$, and wherein $R^{7B}$, $R^{8B}$, $R^{7C}$, and $R^{8C}$ are independently H or methyl.

Embodiment 86

The method, use, or composition defined in any one of embodiments 1-71, wherein E is a bridging group having the formula $-SiR^{7D}R^{8D}-SiR^{7E}R^{8E}-$, wherein $R^{7D}$, $R^{8D}$, $R^{7E}$, and $R^{8E}$ are independently H or any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 87

The method, use, or composition defined in any one of embodiments 1-71, wherein E is a bridging group having the formula $-SiR^{7D}R^{8D}-SiR^{7E}R^{8E}-$, wherein $R^{7D}$, $R^{8D}$, $R^{7E}$, and $R^{8E}$ are independently H or methyl.

Embodiment 88

The method, use, or composition defined in any one of embodiments 1-87, wherein p is equal to 1.

Embodiment 89

The method, use, or composition defined in any one of embodiments 1-87, wherein p is equal to 0.

Embodiment 90

The method, use, or composition defined in any one of embodiments 1-53, wherein the metallocene compound has formula MET-B, or a pharmaceutically acceptable salt thereof:

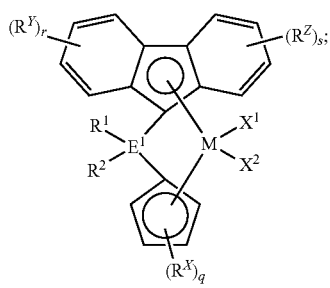

(MET-B)

wherein:

M is Ti, Zr, or Hf;

each $R^X$, $R^Y$, and $R^Z$ independently is H, a halide, hydrocarbyl group, halogenated hydrocarbyl group, oxygen-containing group, sulfur-containing group, nitrogen-containing group, or silicon-containing group;

$E^1$ is C or Si;

$R^1$ and $R^2$ are independently H or a hydrocarbyl group, halogenated hydrocarbyl group, oxygen-containing group, sulfur-containing group, nitrogen-containing group, or silicon-containing group;

$X^1$ and $X^2$ independently are monoanionic ligands; and q, r, and s independently are 0, 1, 2, 3, or 4.

Embodiment 91

The method, use, or composition defined in embodiment 90, wherein $E^1$ is C.

Embodiment 92

The method, use, or composition defined in embodiment 90, wherein $E^1$ is Si.

Embodiment 93

The method, use, or composition defined in any one of embodiments 90-92, wherein $R^1$ and $R^2$ and each $R^X$, $R^Y$, and/or $R^Z$ independently is H or any hydrocarbyl group, halogenated hydrocarbyl group, oxygen-containing group, sulfur-containing group, nitrogen-containing group, or silicon-containing group disclosed herein.

Embodiment 94

The method, use, or composition defined in any one of embodiments 90-93, wherein $R^1$ and $R^2$ and each $R^X$, $R^Y$, and/or $R^Z$ independently is any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 95

The method, use, or composition defined in any one of embodiments 90-94, wherein at least one of $R^1$ and $R^2$ is a phenyl group.

Embodiment 96

The method, use, or composition defined in any one of embodiments 90-95, wherein at least one of $R^1$ and $R^2$ is $C_3$ to $C_8$ terminal alkenyl group.

Embodiment 97

The method, use, or composition defined in any one of embodiments 90-96, wherein $R^1$ and $R^2$ are independently methyl, ethyl, propyl, butyl, pentyl, hexyl, heptyl, octyl, ethenyl, propenyl, butenyl, pentenyl, hexenyl, heptenyl, octenyl, phenyl, tolyl, or benzyl.

Embodiment 98

The method, use, or composition defined in any one of embodiments 90-97, wherein both $R^1$ and $R^2$ are phenyl groups.

Embodiment 99

The method, use, or composition defined in any one of embodiments 90-98, wherein at least one $R^X$, $R^Y$, and/or $R^Z$ independently is a $C_1$ to $C_8$ alkyl group or $C_3$ to $C_8$ alkenyl group.

Embodiment 100

The method, use, or composition defined in any one of embodiments 90-99, wherein at least one $R^X$, $R^Y$, and/or $R^Z$ independently is a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group.

Embodiment 101

The method, use, or composition defined in any one of embodiments 90-93, wherein at least one of $R^1$, $R^2$, $R^X$, $R^Y$, and/or $R^Z$ independently is any $C_1$ to $C_{18}$ halogenated hydrocarbyl group disclosed herein, for example, pentafluorophenyl, trifluoromethyl, etc.

Embodiment 102

The method, use, or composition defined in any one of embodiments 90-93, wherein at least one of $R^1$, $R^2$, $R^X$, $R^Y$, and/or $R^Z$ independently is any oxygen-containing group having up to 18 carbon atoms disclosed herein, for example, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a nitro-phenoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), an acetate group, a trichloroacetate group, a hydrogen maleinate group, a polyol group, a polyethylene glycol (PEG) group, $-OBR^C_2$, $-OSO_2R^C$, $-OCOCH_2NR^C_3X$, or $-OCOCH(Rc)NR^C_3X$, etc., wherein each X independently is any halide disclosed herein and each $R^C$ independently is H or any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 103

The method, use, or composition defined in any one of embodiments 90-93, wherein at least one of $R^1$, $R^2$, $R^X$, $R^Y$, and/or $R^Z$ independently has the formula —$R^DOR^D$ or —$R^D$(CO)O$R^D$, wherein each $R^D$ independently is H or any hydrocarbyl group, halogenated hydrocarbyl group, oxygen-containing group, sulfur-containing group, nitrogen-containing group, or silicon-containing group disclosed herein.

Embodiment 104

The method, use, or composition defined in any one of embodiments 90-93, wherein at least one of $R^1$, $R^2$, $R^X$, $R^Y$ and/or $R^Z$ independently is any sulfur-containing group having up to 18 carbon atoms disclosed herein, for example, a $C_1$ to $C_{18}$ thiocarboxy group, a methylthiolate group, an ethylthiolate group, a phenylthiolate group, an alkylammonium chloride phenylthiolate group, etc.

Embodiment 105

The method, use, or composition defined in any one of embodiments 90-93, wherein at least one of $R^1$, $R^2$, $R^X$, $R^Y$, and/or $R^Z$ independently is any nitrogen-containing group having up to 18 carbon atoms disclosed herein, for example, a $C_1$ to $C_{18}$ hydrocarbylaminyl group, a methylaminyl group, an ethylaminyl group, a propylaminyl group, a phenylaminyl group, a dimethylaminyl group, a di-ethylaminyl group, a di-propylaminyl group, a di-phenylaminyl group, —N(SiMe$_3$)$_2$, —N(SiEt$_3$)$_2$, —N=C=S, an ammonium group (—NR$^C{}_3$X), etc., wherein X is a any halide disclosed herein and each $R^C$ independently is H or a $C_1$ to $C_{18}$ hydrocarbyl group, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 106

The method, use, or composition defined in any one of embodiments 90-93, wherein at least one of $R^1$, $R^2$, $R^X$, $R^Y$, and/or $R^Z$ independently is any silicon-containing group having up to 18 carbon atoms disclosed herein, for example, any $C_1$ to $C_{18}$ hydrocarbylsilyl group disclosed herein, such as trimethylsilyl, triethylsilyl, tripropylsilyl, tributylsilyl, tripentylsilyl, triphenylsilyl, allyldimethylsilyl, etc.

Embodiment 107

The method, use, or composition defined in any one of embodiments 90-106, wherein q, r, and s independently are 0, 1, or 2.

Embodiment 108

The method, use, or composition defined in any one of embodiments 90-107, wherein q, r, and s independently are 0 or 1.

Embodiment 109

The method, use, or composition defined in any one of embodiments 90-108, wherein q is equal to 0.

Embodiment 110

The method, use, or composition defined in any one of embodiments 90-109, wherein r and s are both equal to 0.

Embodiment 111

The method, use, or composition defined in any one of the preceding embodiments, wherein M is Ti.

Embodiment 112

The method, use, or composition defined in any one of embodiments 1-110, wherein M is Zr.

Embodiment 113

The method, use, or composition defined in any one of embodiments 1-110, wherein M is Hf.

Embodiment 114

The method, use, or composition defined in any one of the preceding embodiments, wherein $X^1$ and $X^2$ independently are any monoanionic ligand disclosed herein, for example, H (hydride), BH$_4$, or any halide, hydrocarbyl group, halogenated hydrocarbyl group, oxygen-containing group, sulfur-containing group, nitrogen-containing group, or silicon-containing group disclosed herein.

Embodiment 115

The method, use, or composition defined in any one of embodiments 1-114, wherein $X^1$ and $X^2$ independently are H, BH$_4$, or any halide disclosed herein.

Embodiment 116

The method, use, or composition defined in any one of embodiments 1-114, wherein at least one of $X^1$ and $X^2$ is Cl.

Embodiment 117

The method, use, or composition defined in any one of embodiments 1-114, wherein $X^1$ and $X^2$ are Cl.

Embodiment 118

The method, use, or composition defined in any one of embodiments 1-114, wherein at least one of $X^1$ and $X^2$ independently is any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 119

The method, use, or composition defined in any one of embodiments 1-114, wherein at least one of $X^1$ and $X^2$ independently is a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group, or a benzyl group.

Embodiment 120

The method, use, or composition defined in any one of embodiments 1-114, wherein at least one of $X^1$ and $X^2$ independently is any $C_1$ to $C_{18}$ halogenated hydrocarbyl group disclosed herein, for example, pentafluorophenyl, trifluoromethyl, etc.

Embodiment 121

The method, use, or composition defined in any one of embodiments 1-114, wherein at least one of $X^1$ and $X^2$ independently is any oxygen-containing group having up to 18 carbon atoms disclosed herein, for example, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a nitro-phenoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), an acetate group, a trichloroacetate group, a hydrogen maleinate group, a polyol group, a polyethylene glycol (PEG) group, $-OBR^C_2$, $-OSO_2R^C$, $-OCOCH_2NR^C_3X$, or $-OCOCH(R^C)NR^C_3X$, etc., wherein each X independently is any halide disclosed herein and each $R^C$ independently is H or any $C_1$ to $C_{18}$ hydrocarbyl group disclosed herein, for example, any $C_1$ to $C_{10}$ alkyl group, $C_2$ to $C_{10}$ alkenyl group, $C_4$ to $C_{10}$ cycloalkyl group, $C_6$ to $C_{10}$ aryl group, or $C_7$ to $C_{10}$ aralkyl group disclosed herein.

Embodiment 122

The method, use, or composition defined in any one of embodiments 1-114, wherein at least one of $X^1$ and $X^2$ independently has the formula $-R^DOR^D$ or $-R^D(CO)OR^D$, wherein each $R^D$ independently is H or any hydrocarbyl group, halogenated hydrocarbyl group, oxygen-containing group, sulfur-containing group, nitrogen-containing group, or silicon-containing group disclosed herein.

Embodiment 123

The method, use, or composition defined in any one of embodiments 1-114, wherein at least one of $X^1$ and $X^2$ independently is any sulfur-containing group having up to 18 carbon atoms disclosed herein, for example, a $C_1$ to $C_{18}$ thiocarboxy group, a methylthiolate group, an ethylthiolate group, a phenylthiolate group, an alkylammonium chloride phenylthiolate group, etc.

Embodiment 124

The method, use, or composition defined in any one of embodiments 1-114, wherein at least one of $X^1$ and $X^2$ independently is any nitrogen-containing group having up to 18 carbon atoms disclosed herein, for example, a $C_1$ to $C_{18}$ hydrocarbylaminyl group, a methylaminyl group, an ethylaminyl group, a propylaminyl group, a phenylaminyl group, a dimethylaminyl group, a di-ethylaminyl group, a di-propylaminyl group, a di-phenylaminyl group, $-N(SiMe_3)_2$, $-N(SiEt_3)_2$, $-N=C=S$, etc.

Embodiment 125

The method, use, or composition defined in any one of embodiments 1-114, wherein at least one of $X^1$ and $X^2$ independently is any silicon-containing group having up to 18 carbon atoms disclosed herein, for example, any $C_1$ to $C_{18}$ hydrocarbylsilyl group disclosed herein, such as trimethylsilyl, triethylsilyl, tripropylsilyl, tributylsilyl, tripentylsilyl, triphenylsilyl, allyldimethylsilyl, etc.

Embodiment 126

The method, use, or composition defined in any one of embodiments 1-53, wherein the metallocene compound has formula CPH-1, CPH-2, CPH-3, CPH-4, CPH-5, CPH-6, CPH-7, CPH-8, CPH-9, CPH-10, CPH-11, CPH-12, CPH-13, CPH-14, or CPH-15, or a pharmaceutically acceptable salt thereof, or a combination thereof.

Embodiment 127

The method, use, or composition defined in any one of embodiments 1-53, wherein the metallocene compound has formula CPH-1, or a pharmaceutically acceptable salt thereof.

Embodiment 128

The method, use, or composition defined in any one of embodiments 1-53, wherein the metallocene compound has formula CPH-2, or a pharmaceutically acceptable salt thereof.

Embodiment 129

The method, use, or composition defined in any one of embodiments 1-53, wherein the metallocene compound has formula CPH-3, or a pharmaceutically acceptable salt thereof.

Embodiment 130

The method, use, or composition defined in any one of embodiments 1-53, wherein the metallocene compound has formula CPH-4, or a pharmaceutically acceptable salt thereof.

Embodiment 131

The method, use, or composition defined in any one of embodiments 1-53, wherein the metallocene compound has formula CPH-5, or a pharmaceutically acceptable salt thereof.

Embodiment 132

The method, use, or composition defined in any one of embodiments 1-53, wherein the metallocene compound has formula CPH-6, or a pharmaceutically acceptable salt thereof.

Embodiment 133

The method, use, or composition defined in any one of embodiments 1-53, wherein the metallocene compound has formula CPH-7, or a pharmaceutically acceptable salt thereof.

Embodiment 134

The method, use, or composition defined in any one of embodiments 1-53, wherein the metallocene compound has formula CPH-8, or a pharmaceutically acceptable salt thereof.

Embodiment 135

The method, use, or composition defined in any one of embodiments 1-53, wherein the metallocene compound has formula CPH-9, or a pharmaceutically acceptable salt thereof.

Embodiment 136

The method, use, or composition defined in any one of embodiments 1-53, wherein the metallocene compound has formula CPH-10, or a pharmaceutically acceptable salt thereof.

Embodiment 137

The method, use, or composition defined in any one of embodiments 1-53, wherein the metallocene compound has formula CPH-11, or a pharmaceutically acceptable salt thereof.

Embodiment 138

The method, use, or composition defined in any one of embodiments 1-53, wherein the metallocene compound has formula CPH-12, or a pharmaceutically acceptable salt thereof.

Embodiment 139

The method, use, or composition defined in any one of embodiments 1-53, wherein the metallocene compound has formula CPH-13, or a pharmaceutically acceptable salt thereof.

Embodiment 140

The method, use, or composition defined in any one of embodiments 1-53, wherein the metallocene compound has formula CPH-14, or a pharmaceutically acceptable salt thereof.

Embodiment 141

The method, use, or composition defined in any one of embodiments 1-53, wherein the metallocene compound has formula CPH-15, or a pharmaceutically acceptable salt thereof.

We claim:

1. A method of treating cancer in a subject in need thereof, comprising administering to the subject a composition comprising a therapeutically effective amount of a metallocene compound, and optionally a pharmaceutically acceptable diluent, excipient, or carrier; wherein the metallocene compound has the structure of formula CPH-1, CPH-2, CPH-3, CPH-4, CPH-5, CPH-6, CPH-7, CPH-8, CPH-9, CPH-10, CPH-11, CPH-12, CPH-13, CPH-14, or CPH-15, or a pharmaceutically acceptable salt thereof:

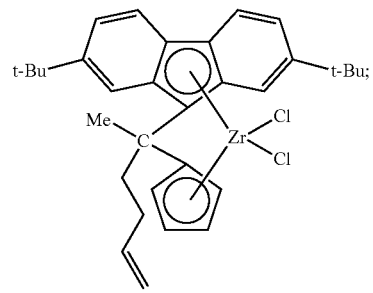

CPH-1

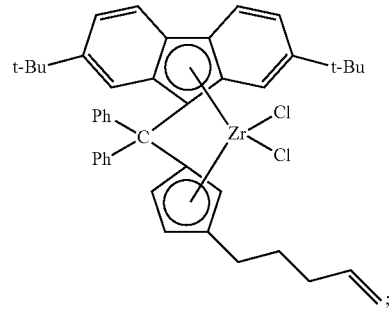

CPH-2

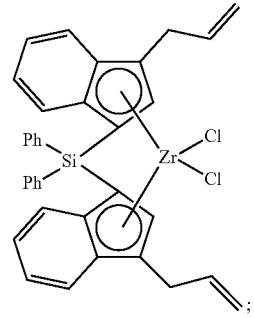

CPH-3

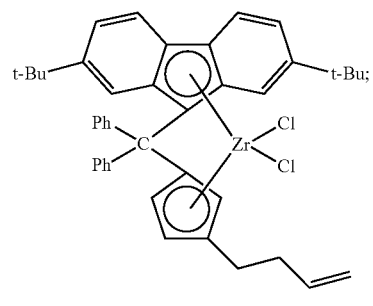

CPH-4

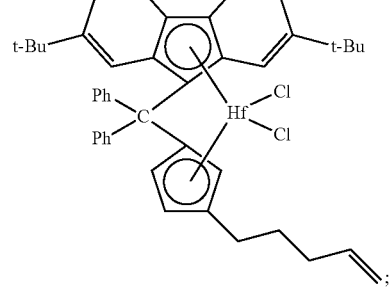

CPH-5

-continued

CPH-6

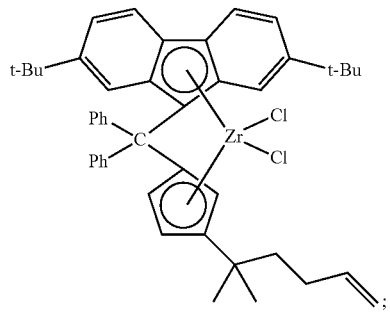

CPH-7

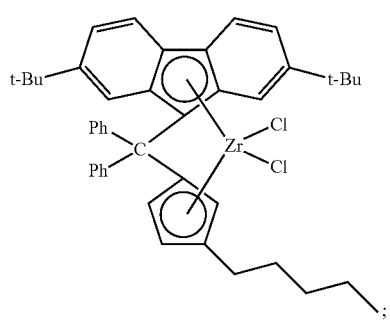

CPH-8

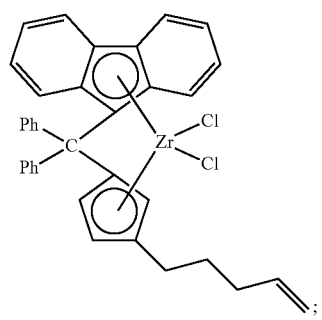

CPH-9

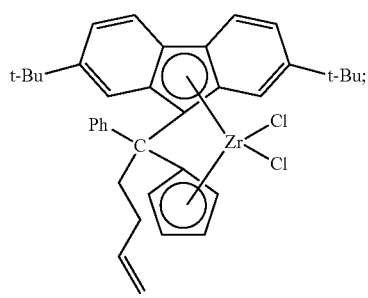

CPH-10

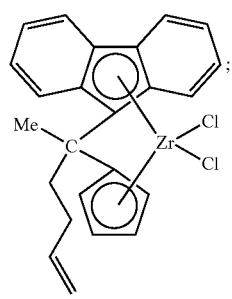

-continued

CPH-11

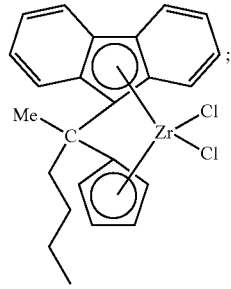

CPH-12

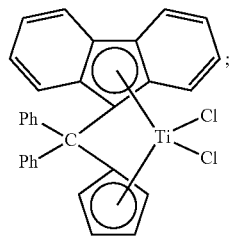

CPH-13

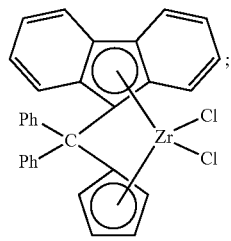

CPH-14

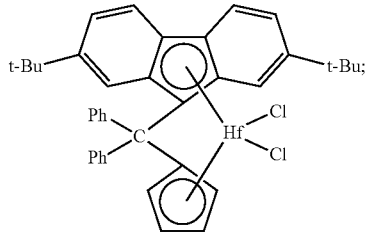

CPH-15

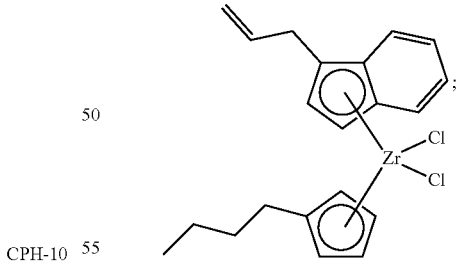

wherein the cancer is melanoma, lung, colon, urinary bladder, breast, renal, prostate, ovarian, cervical, or head and neck cancer.

2. A method of treating cancer in a subject in need thereof, comprising administering to the subject a composition comprising:

a therapeutically effective amount of a metallocene compound having formula MET-B, or a pharmaceutically acceptable salt thereof:

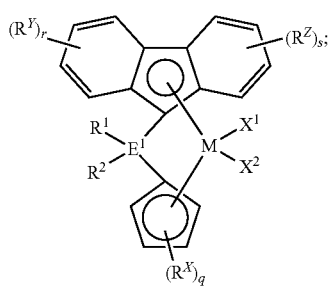

(MET-B)

and
optionally a pharmaceutically acceptable diluent, excipient, or carrier; wherein:
M is Ti, Zr, or Hf;
each $R^X$, $R^Y$, and $R^Z$ independently is H, a halide, hydrocarbyl group, or halogenated hydrocarbyl group;
$E^1$ is C or Si;
$R^1$ and $R^2$ are independently H or a hydrocarbyl group, or halogenated hydrocarbyl group;
$X^1$ and $X^2$ are independently a monoanionic ligand; and
q, r, and s are independently 0, 1, 2, 3, or 4; and
wherein the cancer is melanoma, lung, colon, urinary bladder, breast, renal, prostate, ovarian, cervical, or head and neck cancer.

3. The method of claim 2, wherein the cancer is resistant or insensitive to treatment with one or more of alemtuzumab, aminoglutethimide, anastrozole, asparginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, and/or vorinostat.

4. The method of claim 2, wherein the cancer is resistant or insensitive to treatment with a platinum agent.

5. The method of claim 2, wherein the cancer is resistant or insensitive to treatment with a taxane.

6. The method of claim 1, wherein the subject is a human.

7. The method of claim 2, wherein:
M is Zr or Hf; or
at least one $R^X$, $R^Y$, or $R^Z$ is a $C_1$ to $C_8$ alkyl or $C_3$ to $C_8$ alkenyl group; or
$E^1$ is C; or
at least one of $R^1$ and $R^2$ is an alkyl, alkenyl, or phenyl; or
q, r, and s are independently 0, 1, or 2; or
any combination thereof.

8. The method of claim 2, wherein:
M is Zr or Hf;
at least one $R^X$, $R^Y$, or $R^Z$ is a $C_1$ to $C_8$ alkyl or $C_3$ to $C_8$ alkenyl group;
$E^1$ is C;
at least one of $R^1$ and $R^2$ is a phenyl group or an alkenyl group;
q, r, and s are independently 0 or 1; and
at least one of $X^1$ and $X^2$ is Cl.

9. The method of claim 2, wherein the composition is administered in combination with a therapeutically effective amount of a therapeutic agent, the therapeutic agent comprising alemtuzumab, aminoglutethimide, anastrozole, asparginase, bacillus calmette-guerin, bendamustine, bevacizumab, bicalutamide, bleomycin, bortezomib, brentuximab, cabazitaxel, capecitabine, carboplatin, carmustine, cervarix, cetuximab, cisplatin, cyclophosphamide, cytarabine, dacarbazine, dasatinib, daunorubicin, desarelix, dexamethasone, docetaxel, doxil, doxorubicin, epirubicin, erlotinib, etoposide, everolimus, exemestane, fadrozole, fludarabine, 5-fluorouracil, flutamide, fulvestrant, gardasil, gemcitabine, goserelin, ibritumomab, idarubicin, ifosfamide, il-2, imatinib, inlyta, interferon-alpha, ipilimumab, irinotecan, ixabepilone, lapatinib, lenalidomide, letrozole, leucovorin, leuprolide, lomustine, megestrol acetate, melphalan, methotrexate, 6-mercaptopurine, mitomycin-C, mitoxantrone, nilotinib, nilutamide, oxaliplatin, paclitaxel, panitumumab, pazopanib, pegasparginase, pemetrexed, procarbazine, raloxifene, rituximab, sorafenib, sunitinib, sylatron (Peg), tamoxifen, temozolomide, temsirolimus, thalidomide, thioguanine, thiotepa, topotecan, toremifene, tositumomab, trastuzumab, vemurafenib, vincristine, vinorelbine, vismodegib, vorinostat, or a mixture thereof.

10. The method of claim 9, wherein the therapeutic agent comprises bevacizumab, dacarbazine, docetaxel, 5-fluorouracil, gemcitabine, ipilimumab, paclitaxel, or a mixture thereof.

11. The method of claim 9, wherein the therapeutically effective amount of the metallocene compound administered in combination with the therapeutically effective amount of the therapeutic agent results in a synergistic increase in cytotoxicity.

12. The method of claim 6, wherein the cancer is melanoma.

13. The method of claim 6, wherein the cancer is ovarian cancer.

14. The method of claim 6, wherein the cancer is lung, colon, urinary bladder, renal, prostate, or head and neck cancer.

15. The method of claim 6, wherein the cancer is breast or cervical cancer.

16. The method of claim 2, wherein the subject is a human.

17. The method of claim 16, wherein the cancer is melanoma.

18. The method of claim 16, wherein the cancer is ovarian cancer.

19. The method of claim 16, wherein the cancer is lung, colon, urinary bladder, renal, prostate, or head and neck cancer.

20. The method of claim 16, wherein the cancer is breast or cervical cancer.

* * * * *